United States Patent
Pederson

(10) Patent No.: US 11,478,658 B2
(45) Date of Patent: Oct. 25, 2022

(54) CIRCADIAN RHYTHM ENTRAINMENT USING LIGHT THERAPY TO ENHANCE MEDICATION EFFECTIVENESS

(71) Applicant: Larry V. Pederson, Bellevue, WA (US)

(72) Inventor: Larry V. Pederson, Bellevue, WA (US)

( * ) Notice: Subject to any disclaimer, the term of this patent is extended or adjusted under 35 U.S.C. 154(b) by 0 days.

(21) Appl. No.: 16/638,735

(22) PCT Filed: Sep. 27, 2018

(86) PCT No.: PCT/US2018/053215
§ 371 (c)(1),
(2) Date: Feb. 12, 2020

(87) PCT Pub. No.: WO2019/067781
PCT Pub. Date: Apr. 4, 2019

(65) Prior Publication Data
US 2021/0128942 A1    May 6, 2021

Related U.S. Application Data

(60) Provisional application No. 62/564,261, filed on Sep. 28, 2017.

(51) Int. Cl.
*A61N 5/06*   (2006.01)
*G16H 20/10*   (2018.01)

(52) U.S. Cl.
CPC .......... *A61N 5/0618* (2013.01); *G16H 20/10* (2018.01); *A61N 2005/0626* (2013.01)

(58) Field of Classification Search
CPC .......... A61N 5/0618; A61N 2005/0626; A61N 2005/0663; A61N 5/0613; G16H 20/10;
(Continued)

(56) References Cited

U.S. PATENT DOCUMENTS 6,350,275 B1   2/2002   Vreman et al.
2003/0125662 A1   7/2003   Bui
(Continued)

FOREIGN PATENT DOCUMENTS

CN   102448372 A   5/2012
CN   105431201 A   3/2016
(Continued)

OTHER PUBLICATIONS

Chinese Office Action issued for CN Application No. 202010298011.8, Applicant: Larry Pederson, dated Mar. 1, 2021, 5 pages.
(Continued)

*Primary Examiner* — Brian T Gedeon
*Assistant Examiner* — Joshua Andrew Schum-Houck
(74) *Attorney, Agent, or Firm* — Perkins Coie LLP

(57) ABSTRACT

A circadian rhythm entrainment platform can use medication circadian profiles that include mappings of medications to circadian rhythm disruptions and can make conversions of such circadian rhythm disruptions to administrations of light therapy to adjust for the disruptions. The circadian rhythm entrainment platform can specify how to entrain a patient's circadian rhythm using light therapy to compensate for or anticipate side effects of medications and for optimizing medication schedules for a patient's circadian rhythm so as to minimize side effects and increase medication effectiveness. The circadian rhythm entrainment platform can also gather information on the effects of medications on circadian rhythms and interact with patients, medical providers, and other providers in relation to light therapy.

20 Claims, 14 Drawing Sheets

(58) Field of Classification Search
CPC ........ G16H 20/70; G16H 20/30; G16H 50/20; G16H 70/40; G16H 20/40; G16H 10/20; A61B 5/0002; A61B 5/4848; A61B 5/4836; A61B 5/4815; A61B 5/4809; A61B 5/4812; A61B 5/4806; A61M 21/02; A61M 2021/0044; H04L 67/02; H04L 67/12; H04L 67/42
See application file for complete search history.

(56) References Cited

U.S. PATENT DOCUMENTS

| | | |
|---|---|---|
| 2007/0142864 A1 | 6/2007 | Libbus et al. |
| 2008/0220092 A1 | 9/2008 | Dipierro et al. |
| 2012/0296400 A1 | 11/2012 | Bierman et al. |
| 2013/0301034 A1 | 11/2013 | Olds et al. |
| 2016/0034671 A1* | 2/2016 | Hyde .................. G16H 20/70 705/3 |
| 2016/0193442 A1 | 7/2016 | Adamczyk et al. |
| 2016/0381763 A1* | 12/2016 | Loeb .................. H05B 47/105 315/297 |
| 2017/0246086 A1* | 8/2017 | Jain .................... A61J 7/0481 |

FOREIGN PATENT DOCUMENTS

| | | |
|---|---|---|
| WO | 2014210588 A1 | 12/2014 |
| WO | 2017146525 A1 | 8/2017 |
| WO | 2019067781 | 4/2019 |

OTHER PUBLICATIONS

Extended European Search Report, PCT Application No. PCT/US2018/053215 dated May 19, 2021, 10 pages.

International Search Report and Written Opinion, Application No. PCT/US2018/053215 dated Nov. 23, 2018, 10 pages.

Lam et al. "Efficacy of Bright Light Treatment, Fluoxetine, and the Combination in Patients With Nonseasonal Major Depressive Disorder," JAMA Psychiatry, vol. 73, No. 1, Jan. 2016, American Medical Association, p. 56-63.

Niederhofer et al. "Bright Light Treatment as Add-On Therapy for Depression in 28 Adolescents: A Randomized Trial," Primary Care Companion CNS Discord, 4 pages.

* cited by examiner

CIRCADIAN RHYTHM ENTRAINMENT USING LIGHT THERAPY TO ENHANCE MEDICATION EFFECTIVENESS

CROSS-REFERENCE TO RELATED APPLICATIONS

This application claims priority to U.S. Provisional Patent Application No. 62/564,261, titled "Circadian Rhythm Entrainment Using Light Therapy and Melatonin Assay to Enhance Medication Efficacy," filed Sep. 28, 2017, which is herein incorporated by reference in its entirety.

TECHNICAL FIELD

The present disclosure is directed to technologies for optimizing a patient's circadian rhythm through light therapy to reduce medication side effects and enhance medication effectiveness. More particularly, the present disclosure is directed to entraining a patient's circadian rhythm using light therapy, determining aspects of such light therapy individualized for both patients and medications, and related technologies for interacting with patients and various providers in relation to such entrainment.

BACKGROUND

Many serious health concerns plaguing broad segments of society today stem from a fundamental disruption to our daily circadian rhythm (our internal "body clock") due largely to our modern lifestyle.

There are many environmental cues that serve to regulate the human body clock, however the two strongest external cues are exposure to "light" in the morning (particularly light in the blue portion of the visible spectrum i.e. the peak wavelength of sunlight), and exposure to "dark" at night (i.e., absence of light, particularly in the blue portion of the spectrum).

Unlike our ancestors who spent their time primarily outdoors during the day and slept in a completely dark environment at night, most people today spend their days indoors with limited exposure to direct sunlight, particularly in the first 1-2 hours after waking, and are routinely exposed to bright light at night from an array of electronic devices (TV's, computers, tablets, smartphones, etc.) which emit a high percentage of light in the blue portion of the spectrum. Without the predictable, consistent environmental cues of bright light first thing upon waking each morning, and complete darkness at night, the human body clock becomes confused and 'out of sync' with its innate 'day/night light/dark' routine that humans evolved to respond to over millions of years.

This circadian disruption wreaks havoc on many different rhythms in the human body critical to health, including the wake/sleep cycle, digestion, metabolism, immune system, blood pressure, core body temperature, and cell division, among many others. All of these cycles and systems are controlled by the master "body clock" located in the suprachiasmatic nucleus ("SCN") in the brain. (The SCN in turn communicates with 'secondary clocks' located in various organs, and, as has been demonstrated recently, this communication continues right down to the cellular level. Every cell in the body contains its own 'circadian clock' that responds to the master clock in the SCN, much like musicians in a symphony orchestra respond to and follow the lead of the conductor.) These widespread circadian disruptions so prevalent today are now believed to be responsible for, or at a minimum contribute to, many of the diseases that are at epidemic levels in society such as cancer, cardiovascular disease, obesity, circadian sleep disorders, and depression, among others. Additional information on how disruption to a patient's circadian rhythm can contribute to health problems can be found in "*Disruption of Circadian Rhythm Increases the Risk of Cancer, Metabolic Syndrome and Cardiovascular Disease*" by Vignesh Shanmugam et. al., Journal of Local and Global Health Science 2013:3, available at http://www.qscience.com/doi/abs/10.5339/ilghs.2013.3, which is herein incorporated by reference in its entirety.

This circadian disruption compromises the body's ability to effectively and efficiently harness the beneficial effects of peak melatonin secretion at 'night', namely the restorative activities that occur nightly in the body with a well-entrained circadian rhythm, and further, which enable the body's immune system to function optimally to combat maladies ranging from less serious infections to more serious diseases.

Melatonin is commonly known as the 'sleep hormone'—but it is well documented to have a much more crucial function: it acts as the body's "garbage collector", going into every cell in the body every night to remove 'free radicals' (the pre-cursors of cancer and other diseases). All of the repair work that occurs in the human body—right down to the cellular level and this 'free radical' repair—occurs when an individual is sleeping. More particularly, this internal repair work only occurs when an individual's melatonin is at its maximum peak level for a minimum of four hours uninterrupted—a period referred to as 'restorative sleep'. It is during this 'restorative' sleep period that melatonin, which is secreted by the pineal gland in the brain, reaches its maximum level in the bloodstream.

In an individual who has a well-entrained or 'optimized' circadian rhythm with a healthy, 'normal' wake/sleep 'light/dark' cycle, and who thus regularly experiences the desired peak melatonin level, and thus 'restorative' sleep on a nightly basis, this repair work occurs regularly and consistently, and that individual's body can—and typically does—heal itself. In the opposite case, for an individual with a disrupted circadian rhythm, the repair work does not occur on a regulated, nightly basis, and the individual's ability to heal the body is compromised. This out of sync body clock, in turn, can seriously impair an individual's ability to best utilize a medication being administered to combat a disease.

In numerous disease slates, including various cancers, efficacy of medications and other treatments e.g. radiation in human clinical trials has been limited i.e., study results show the drug or treatment is only marginally more effective than placebo ("control"). Many of these drugs and treatments also trigger a wide range of side effects, some of which can be dangerous, even life-threatening. In some cases, the side effect(s) are sufficiently severe that patients elect to discontinue treatment rather than continue to suffer the side effect(s).

Discontinuing treatment of a medication prior to completing the full course of treatment as prescribed at the very least halts any beneficial effects of the medication, rendering it less effective than intended or desired. For some patients, such as those suffering from life-threatening diseases, stopping treatment prematurely can have a lethal outcome.

The most commonly reported (>75%) severe side effect for cancer patients is cancer-related fatigue ("CRF"). CRF is unlike general tiredness and does not resolve after sleeping or resting, nor after the treatment is discontinued-lasting for as long as five years post-treatment for some patients. CRT is unrelenting, pernicious and overwhelming, and is often referred to as 'permanent jet lag'. It is theorized that CRF may be due to a profound disruption of tire patient's internal body clock triggered by the cancer itself, or more probably, by the medication(s) and/or treatment(s) being administered. CRF has historically proven to be treatment-resistant, with all manner of pharmaceutical and behavioral interventions failing to achieve significant relief for the patient.

Chronotherapy is an emerging field of study on the effects of adjusting the timing of administration of medications to improve effectiveness and reduce side effects. To date, researchers have demonstrated positive results in animal studies and in small human clinical trials, however implementation in clinical practice still remains largely impractical. Currently, the majority of patients receive a general or vague recommendation from pharmaceutical manufacturers or prescribing physicians as to timing of medications, e.g., "take twice per day;" "take with food;" or "take at bedtime." Some medications, particularly those administered in a clinical setting e.g., chemotherapy drugs, include recommendations regarding timing e.g., "to be administered at the same time every 24 hours or 7 days." However, these recommendations are intended primarily to maintain a consistent therapeutic level of the drug in the patient's body over time. Little regard is paid by manufacturers, physicians, or patients themselves to the status of a patient's circadian rhythm before, during, or after the treatment period when the medication or treatment is being administered.

Devices and systems exist for determining and adjusting a patient's circadian rhythm. Light therapy devices, such as Litebook EDGE by The Litebook Company Ltd., goLITE BLU by Koninklijke Philips N.V., and HappyLight Lucent by Verilux, are known to shift the user's circadian rhythm either ahead or back by exposing the user's eyes to the device's light output which has a peak intensity in the blue range of the visible spectrum. One way to determine a patient's current circadian rhythm is by measuring an amount of melatonin in the patient's system at various points throughout a day. A salivary melatonin assay kit can be used to make this type of measurement. Unfortunately, the process to determine the patient's circadian rhythm through salivary melatonin assay is cumbersome and not convenient for patients as it requires several samples be collected over multiple days followed by laboratory analysis.

Recently, devices worn on the wrist or elsewhere on the body, or alternatively bed-mounted devices, referred to collectively as 'sleep trackers' or 'activity trackers' are able to accurately monitor and record various biometrics and activities of the wearer, such as periods of sleep (including specific sleep phases e.g. REM), sleep onset, sleep offset, heart rate, body temperature, etc., as well as, in the case of body-mounted devices, periods of activity, non-nighttime sleep periods, etc.

BRIEF DESCRIPTION OF THE DRAWINGS

The techniques introduced herein may be better understood by referring to the following Detailed Description in conjunction with the accompanying drawings, in which like reference numerals indicate identical or functionally similar elements.

DETAILED DESCRIPTION

Figure 1:
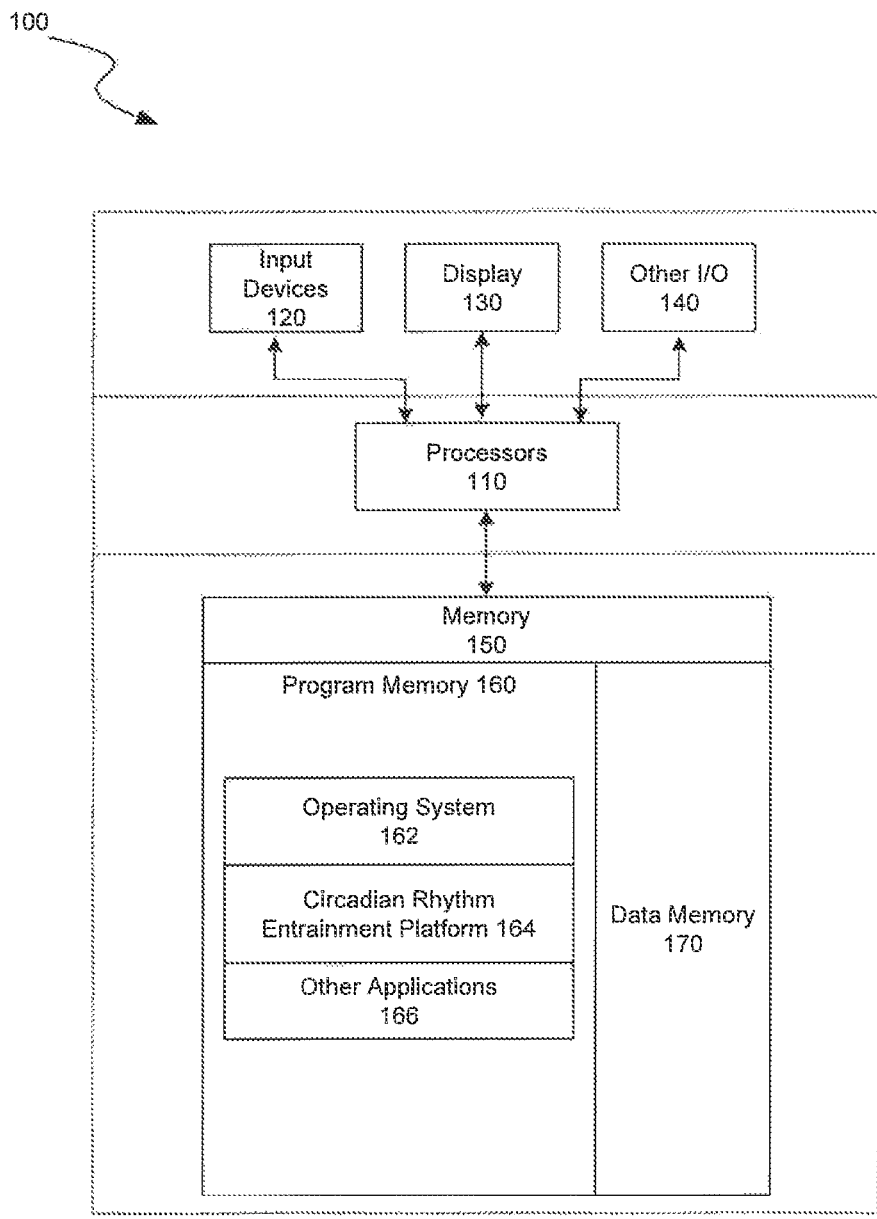
FIG. 1 is a block diagram illustrating an overview of devices on which some implementations of the present technology can operate.

The present disclosure is directed to technologies for enhancing medication effectiveness through properly timed administration of light therapy to improve a patient's circadian rhythm prior to commencing medication treatment, and for adjusting a patient's circadian rhythm during and following treatment to account for and offset medication side effects disruptive to that patient's circadian rhythm. More particularly, embodiments are disclosed for determining and storing mappings of medications to circadian rhythm adjustments and making conversions of such circadian rhythm adjustments to administrations of light therapy. Further embodiments are disclosed for identifying a patient's circadian rhythm. In addition, embodiments are disclosed for entraining a patients circadian rhythm using light therapy to compensate for or anticipate effects of medications and for optimizing medication schedules for a patient's circadian rhythm. Yet further embodiments are disclosed for computing systems to gather information on the effects of medications on circadian rhythms and to interact with patients, medical providers, and other providers in relation to medications and light therapy.

Overview

One application of the disclosed technology helps alleviate side effects some medications cause due to a disruption of patients' circadian rhythms or to sub-optimal timing of medication administration in relation to patients' circadian rhythms. For example, many cancer treatments including chemotherapy, radiation and prescription drugs/medications, have severe, chronic, often debilitating and intolerable fatigue as a side effect due to disruptions in patients' circadian rhythms.

"Medications," as used herein, can refer to one or more medications/drugs, medical 'non-drug' treatments e.g. radiation, or some combination thereof and the like prescribed by a doctor as a single, one-time treatment or as an ongoing, recurring administration or course of treatment, as well as over-the counter medications/drugs, supplements, etc. "Medications" can also refer to other substances which can affect a circadian rhythm, such as alcohol, cigarettes, air pollution, etc. "Entrainment," as used herein, refers to synchronization to a particular rhythm. "Efficacy," and "effectiveness" as used herein, refer a medication's performance under 'real-world' conditions.

In some cases, the above and other embodiments are carried out or facilitated with a circadian rhythm entrainment platform. A circadian rhythm entrainment platform can include one or more of a desktop or mobile application, a website or other cloud-based environment, or interfaces to medical provider systems, insurance systems, medication databases, government agencies, third-party applications (e.g., calendar, email, sleep tracker, etc.), or to other devices (e.g., a light therapy device, activity tracker, melatonin assay device, etc.). Additional details regarding a circadian rhythm entrainment platform are provided below in relation to FIGS. 1 and 2.

In various implementations, effects of one or more particular medications on multiple patients' circadian rhythms can be analyzed to determine a mapping of the one or more medications to circadian rhythm disruptions. Such a mapping is referred to herein as a "circadian profile" for the particular one or more medications. A circadian rhythm "disruption," as used herein, refers to an alteration in a circadian rhythm such as a shift in peak melatonin, an increase or decrease in melatonin amounts, etc. In some implementations, these circadian profiles can be based on data gathered from one or more of the following: medication clinical trials, including study participant specifics (e.g. age, gender, weight index, other disease states, etc.) and sleep tracker data and/or sleep diaries from study participants, patient feedback to medical providers in clinical practice, or data gathered through patients' use of the disclosed circadian rhythm entrainment platform. The circadian profile for a particular medication may be unique to that medication, and it may be revised and refined over time as additional relevant data becomes available. Identified disruptions can be for a circadian rhythm curve as a whole or can be for particular points or sections in the circadian rhythm curve. For example, a circadian profile for a particular medication can specify that, for a particular course of treatment with that medication, commencing in or about Week 3 of the treatment, a patient's nighttime melatonin peak that pre-treatment occurred consistently between 3:00 am to 5:00 am tends to shift later by three hours, to a peak between 6:00 am and 8:00 am, and additionally, the patient's nighttime Dim Light Melatonin Onset ("DLMO") also shifts later by a similar three hour period. In another example, a circadian profile can specify that, within one week of commencing a particular course of medication, a patient's nighttime melatonin peak that pre-treatment was consistently between 3:00 am to 5:00 am tends to become significantly disrupted such that the nighttime melatonin peak (i.e. "normal" pre-treatment) is replaced by a flattened, more-or-less constant secretion of melatonin over the 24-hour period i.e. during both daytime and nighttime hours. Identified shifts can also be specified for particular timing of medication administration, such as an identification of a two-hour shift later in the six hours following a particular medication that is taken twice weekly.

These circadian profiles can be stored as data structures indexed by medication identifier and specifying one or more expected disruptions or alterations the medication is expected to have on a patient's circadian rhythm. In various implementations, the data structure can include modifiers specifying adjustments to the expected circadian rhythm disruptions for particular situations, such as dosage of the medication prescribed, medication administration schedule (e.g. timing and duration), interactions with other medications, and/or patient specifics (e.g., age, gender, lifestyle or stressors, weight index, other disease states, etc.). The data structures can be applicable as input for an algorithm (discussed below) that can convert the circadian profile mapping to a prescribed regimen of light therapy to prevent or correct disruptions of the patient's circadian rhythm from a normal cycle. In some implementations, input to the algorithm can also include an identification of the patient's current circadian rhythm. Adjusting a circadian rhythm to be more similar to an optimal circadian rhythm is referred to herein as "normalizing" or "entraining" or "optimizing" the patients circadian rhythm. Additional details regarding generating and storing medication circadian profiles are provided below in relation to FIG. 3.

Figure 9:
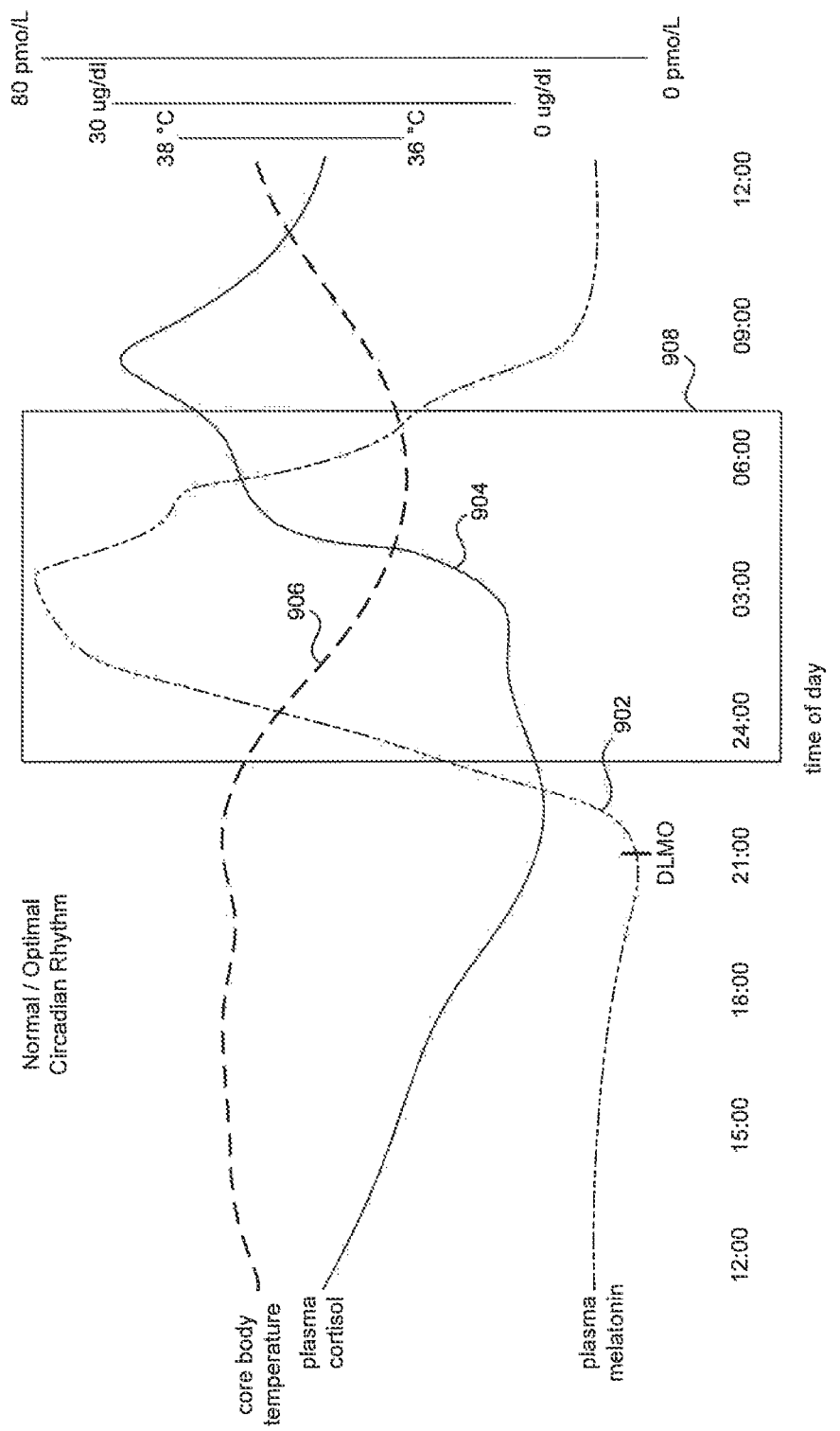
FIGS. 9-13 are conceptual diagrams illustrating an example change in a circadian rhythm due to a light therapy regimen.
Figure 13:
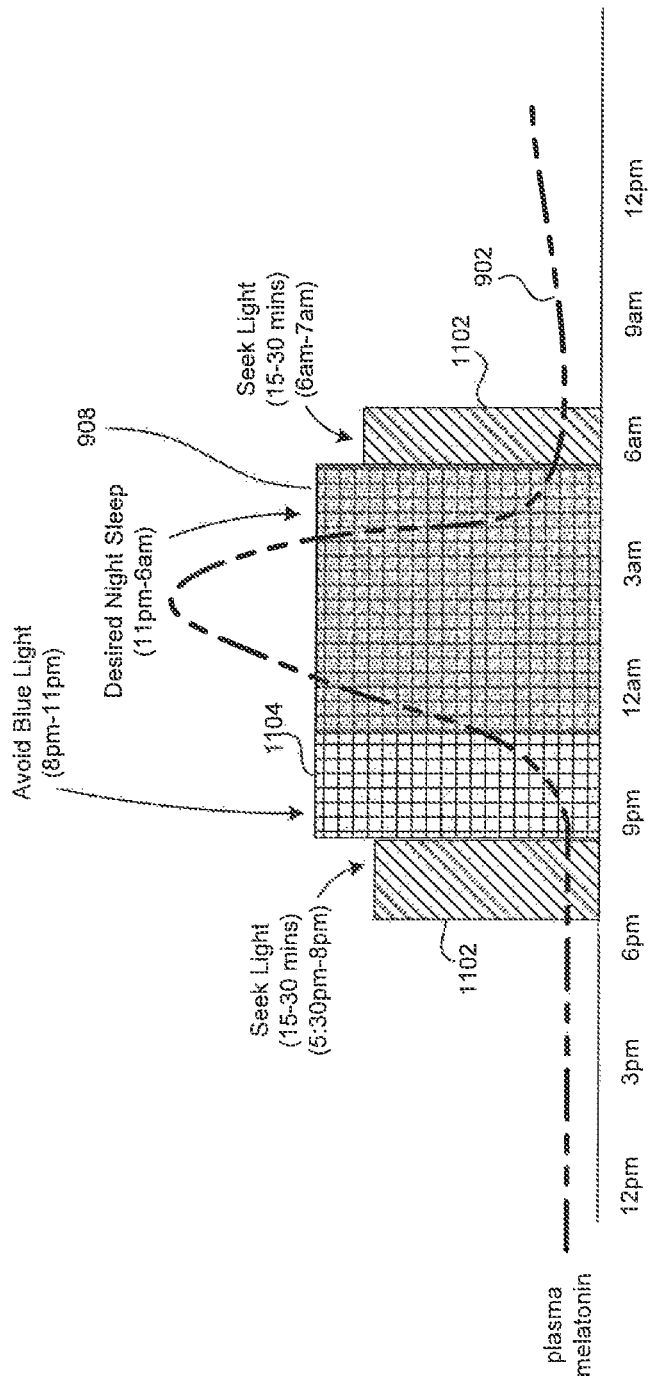

A system can determine a patients current circadian rhythm using one of several algorithms, including plotting measured melatonin levels or mapping (A) sleep activities, other tracked activities, and/or patient input (e.g., responses to questions, sleep diaries, etc.) to (B) aspects of a circadian rhythm. Melatonin is present in, and may be collected from plasma, urine, or saliva. Various assay systems and devices can be used by a patient to collect melatonin measurements over a period of time, such as periodically over a 24-72 hour time window. These measurements can be plotted, e.g., with time on the x-axis and melatonin level on the y-axis and these plots can be fitted to a circadian rhythm curve for the patient. This curve can include identification of the patients Dim Light Melatonin Onset ("DLMO"), recognized as the most precise and reliable marker for determining a patient's circadian rhythm, as well as their sleep-wake cycle. A "normal" circadian rhythm curve, as shown in FIGS. 9 and 13, generally has a "peak" level of melatonin between 1 am-5 am, and a "trough," i.e., suppressed level of melatonin between 9 am-9 pm, with a DLMO generally between 9 pm-10 pm.

In some implementations, direct melatonin measurements may be too difficult to obtain or may be otherwise unavailable. The disclosed technology can instead obtain a patient's circadian rhythm by extrapolating from available data gathered for the patient. As previously referenced, mobile phones, fitness trackers, and 'smart' watches, available commercially, are able to track sleep/wake patterns and disruptions, amount of activity, heart rate, and other biometric factors over time. This information can be supplied to a circadian rhythm entrainment platform, e.g. via Bluetooth® or other such communication technologies. In addition, patients can input data to the circadian rhythm entrainment platform, e.g., specifying their sleep pattern and disruptions, various pulse measurements, etc. The circadian rhythm entrainment platform can transform this biometric data into a circadian rhythm for the patient. For example, the circadian rhythm entrainment platform can have data gathered on sleep activity or other biometrics associated with melatonin measured circadian rhythms for various patients. This data can provide a mapping for determining an expected circadian rhythm based on the patient's biometrics. In some implementations, this mapping can take the form of a machine learning model such as a neural network, trained using the known associations between biometrics and circadian rhythms. When the circadian rhythm entrainment platform applies the model to biometrics for a patient, it can produce a circadian rhythm expected for the patient. Additional details regarding determining a patient's circadian rhythm are provided below in relation to FIG. 4.

The circadian rhythm entrainment platform can provide a prescribed regimen of light therapy during a course of medication and, in some cases, can also provide prescribed light therapy regimens before beginning the medication, in order to adjust a patient's rhythm prior to commencing the medication. This could be the case when, for example, a patient's circadian rhythm is not optimized due to one or more of a variety of causes including health issues, sleep disorders, poor sleep hygiene, work schedules, lifestyle, jet lag, etc. As used herein, an "adjustment" for a circadian rhythm can be any determined change for or to a patient's circadian rhythm, such as a shift in melatonin peak and/or trough times, a change to an amount of melatonin produced by the body, or another change. In some implementations, before a patient begins medication, the circadian rhythm entrainment platform can use the circadian rhythm for the patient and the circadian profile(s) of the prescribed medication(s) to determine an expected disruption of the patient's circadian rhythm once the patient commences the medication(s). The circadian rhythm entrainment platform can convert this expected disruption into an adjustment that can be accomplished by a prescribed regimen of one or more light therapy treatments (e.g. daily) to change the patient's circadian rhythm so as to pre-compensate for the expected disruption while the patient is on the medication. In other implementations, the circadian rhythm entrainment platform can determine a light therapy treatment regimen to normalize the patient's circadian rhythm prior to commencing a course of medication. Normalization of a circadian rhythm using light therapy is illustrated in greater detail below with reference to FIGS. 9-13.

The circadian rhythm entrainment platform can apply one or more transformation functions configured to output indications of suitable light therapy regimen(s) based on either a received desired amount and direction of circadian rhythm shift or adjustment, or a received patient's current circadian rhythm and a desired circadian rhythm or specified changes to the circadian rhythm. This transformation function can be generated based on clinical research data on how patients' circadian rhythms are affected by various regimens of light therapy. The light therapy regimen can specify how to 'advance' or 'delay' the circadian rhythm curve peak to align with a normal or pre-shifted curve. Alternatively, in the instance of a circadian rhythm that is disrupted to the extent that the 'normal' peak and trough curve is no longer apparent, the regimen can specify how to administer light therapy treatments to re-establish the 'peak' and 'trough' and normalize the rhythm. The light therapy regimen can specify an amount of time to receive light therapy at a particular radiance, and/or to avoid light in particular spectrums, at what time(s) and for what durations, and at what recurring frequency. In some implementations, the prescribed light therapy regimen can be updated as new information about the patient's current circadian rhythm are received and based on how the patient is responding to ongoing light therapy treatments.

When the patient's circadian rhythm has been pre-shifted, as indicated by a measurement of their circadian rhythm or based on their completion of the prescribed light therapy regimen, such that the patient's rhythm is indicated to be in the 'normal' range, the patient can commence the medication. In some implementations, a patient's health care provider and/or insurance provider may require the patient's circadian rhythm to be optimized prior to, respectively, authorizing a particular medication or providing coverage for same. In such an instance, data gathered by the circadian rhythm entrainment platform may be transmitted from the platform to the patient's medical provider, insurer, etc. as required. In some implementations, for example, the patient begins medication having pre-shifted their circadian rhythm to 'normal' pre-treatment and disruption of their rhythm occurs as a side effect of the medication. As the medication course progresses, the circadian rhythm entrainment platform can provide a prescribed 'during-medication' light therapy regimen. For example, when the medication begins having an effect on the patient, a different light therapy regimen can be prescribed than the one prescribed to pre-shift the patient's circadian rhythm. Similarly, a patient who has not pre-shifted their circadian rhythm pre-treatment and has commenced the course of medication, finds their circadian rhythm to be disrupted during treatment. The circadian rhythm platform can provide a prescribed 'during-medication' light therapy regimen to adjust the patient's circadian rhythm to normal.

The circadian rhythm entrainment platform can determine this light therapy regimen based on one or more of the following: an expected effect of taking the medication as specified in the medication's circadian profile, updated data on the patient's current circadian rhythm, input from the patient on perceived medication side effects, information on timing and dosage of the medication the patient is taking, and information on the patient's adherence to previous light therapy regimens. Additional details regarding entraining a patient's circadian rhythm prior to and during a course of medication are provided below in relation to FIG. 5.

Throughout the pre-medication phase, during-medication phase, and also in a post-medication phase, the circadian rhythm entrainment platform can gather information on the effects of medications on circadian rhythms and can interact with patients, medical and other providers, and third-party systems in relation to circadian rhythm entrainment. Examples of the data gathering aspects include obtaining one or more of: patient profile and medication information, medication circadian profiles, data for determining a patient's circadian rhythm (e.g., melatonin measurement, sleep and wake activity, etc.), mappings of circadian rhythms and medication circadian profiles to prescribed circadian rhythms or circadian rhythm disruptions, mappings of prescribed circadian rhythms or circadian rhythm disruptions to light therapy regimens, and indications of patient feedback on medication(s), light therapy use, and side effect reports. Data gathered by the circadian rhythm entrainment platform can be stored, for example, locally on a patient's electronic device or in a designated repository such as through a medical provider, a medical tracking service, servers for the circadian rhythm entrainment platform, or databases used to update medication circadian profiles. Proper patient consent and anonymization fox sharing patient data or compliance with regulations for storing patient data can be observed.

Examples of the interaction aspects of the circadian rhythm entrainment platform include: providing interfaces such as Application Programming interfaces (APIs), Graphical User Interfaces (GUI), shared access to repositories (e.g., reading/writing to a database that other systems can read/write to), and making calls to such interfaces provided by other systems. More specifically the circadian rhythm entrainment platform can provide APIs and GUIs for patients and medical providers to receive information such as the examples noted above and to interface with other devices and programs such as sleep/activity trackers, calendar applications, notification systems, etc., and to provide information to other entities such as to update medication circadian profiles, medical providers, insurance providers, manufacturers of relevant medications, light therapy devices, sleep/activity tracker devices, FDA, etc. In some implementations, the circadian rhythm entrainment platform can provide patient notifications (e.g., through a mobile app, messaging service, adding calendar items, etc.) for features such as: reminders to take circadian rhythm readings, reminders to take medications, reminders to perform light therapy, reminders to avoid blue light, reminders to sleep, identified changes in circadian rhythm, medical appointment reminders, etc. Additional details regarding the circadian rhythm entrainment platform's information gathering features and providing output and interactions are provided below in relation to FIG. 6.

Despite the importance of maintaining a normal circadian rhythm for health, existing systems for administering medications fail to account for the status of a patient's circadian rhythm before commencing treatment, or for the effect(s) of medication(s) on a patient's circadian rhythm during and after treatment. Further, existing light therapy systems fail to provide treatment to improve medication effectiveness, or to reduce medication side effects beyond results in a handful of pilot clinical trials. In particular, current systems fail to enable a patient to: (i) determine their accurate, real-time circadian rhythm in a timely, convenient, practical manner, (ii) understand how to adjust their current circadian rhythm to the 'desired' or 'optimal' circadian rhythm prior to commencing a course of treatment, (iii) understand the degree of disruption to their circadian rhythm caused or expected from one or more specific medications or treatments, (iv) factor this knowledge into a light therapy regimen(s) to optimize their body clock prior to, during, or following administration of medication or treatment, and (v) have a means to monitor and confirm when the desired adjustment to their circadian rhythm has occurred and that it is being sustained, both during and after the course of medication or treatment is completed.

The inventor has recognized a need to improve the entrainment of patients' circadian rhythms prior to commencing a course of medication as well as during a course of medication in order to enhance the effectiveness of those medications. Further, there is a need to increase the degree of tolerance by patients of side effects of many medications and treatment. Increased tolerance could lead to improved compliance of prescribed treatments, which in turn may increase effectiveness of these treatments and ultimately improve outcomes for patients.

The circadian rhythm entrainment platform and associated systems of the current invention provide improvements that are expected to address these failures in existing systems by employing the embodiments described herein. These embodiments serve to improve the entrainment of a patient's circadian rhythm, in turn reducing negative side effects, improving compliance with a course of treatment, and increasing medication effectiveness. In addition, the described embodiments also enable patients to understand how and when to use light therapy to achieve these results, provide communications to help patients interact with the circadian rhythm entrainment platform, correctly administer light therapy and adhere to their medication(s) treatment plan, and interface with medical providers, insurers, medication manufacturers, light device manufacturers, Food & Drug Administration, and other relevant parties. Some of the benefits achieved for patients through these embodiments include, for example, a more optimized circadian rhythm i.e. a regulated sleep/wake cycle, improved 'wake' cycle characteristics (e.g., alertness, mood, performance, appetite, metabolism, etc.), improved sleep cycle (e.g., consistency of sleep onset, sleep duration and sleep offset, proper 'restorative' sleep, waking feeling rested, etc.), improved immune function, reduction or elimination of medication side effects, improved compliance with and adherence to medication and/or treatment regimens, reduced early cessation rates for medication and/or treatment regimens, and ultimately overall increased effectiveness of medications and improved patient outcomes.

Example Suitable Environment

Several implementations are discussed below in more detail in reference to the figures. FIG. 1, for example, is a block diagram illustrating an overview of devices on which some implementations of the disclosed technology can operate. The devices can comprise hardware components of a device 100 that can implement at least part of a circadian rhythm entrainment platform. Device 100 can include one or more input devices 120 that provide input to the Processor(s) 110 (e.g., CPU(s), GPU(s), HPU(s), etc.), notifying it of actions. The actions can be mediated by a hardware controller that interprets the signals received from the input device and communicates the information to the processors 110 using a communication protocol. Input devices 120 include, for example, a mouse, a keyboard, a touchscreen, an infrared sensor, a touchpad, a wearable input device, a camera- or image-based input device, a microphone, or other user input devices.

Processors 110 can be a single processing unit or multiple processing units in a device or distributed across multiple devices. Processors 110 can be coupled to other hardware devices, for example, with the use of a bus, such as a PCI bus or SCSI bus. The processors 110 can communicate with a hardware controller for devices, such as for a display 130. Display 130 can be used to display text and graphics. In some implementations, display 130 provides graphical and textual visual feedback to a user. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network card, video card, audio card, USB, fire-wire or other external device, camera, printer, speakers, CD-ROM drive, DVD drive, disk drive, or Blu-Ray device.

In some implementations, the device 100 also includes a communication device capable of communicating wirelessly or wire-based with a network node. The communication device can communicate with another device or a server through a network using, for example, TCP/IP protocols. Device 100 can utilize the communication device to distribute operations across multiple network devices.

The processors 110 can have access to a memory 150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 150 can include program memory 160 that stores programs and software, such as an operating system 162, circadian rhythm entrainment platform 164, and other application programs 166.

Memory 150 can also include data memory 170 that can include medication circadian profile data structures, patient profile data, patient circadian rhythm data, medical provider data, rules for transforming circadian rhythm data and circadian profile data into circadian rhythm adjustment data; mappings of circadian rhythm adjustment data into a prescribed light therapy regimen, GUI components, templates for user notifications, configuration data, settings, user options or preferences, etc., which can be provided to the program memory 160 or any element of the device 100.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2:
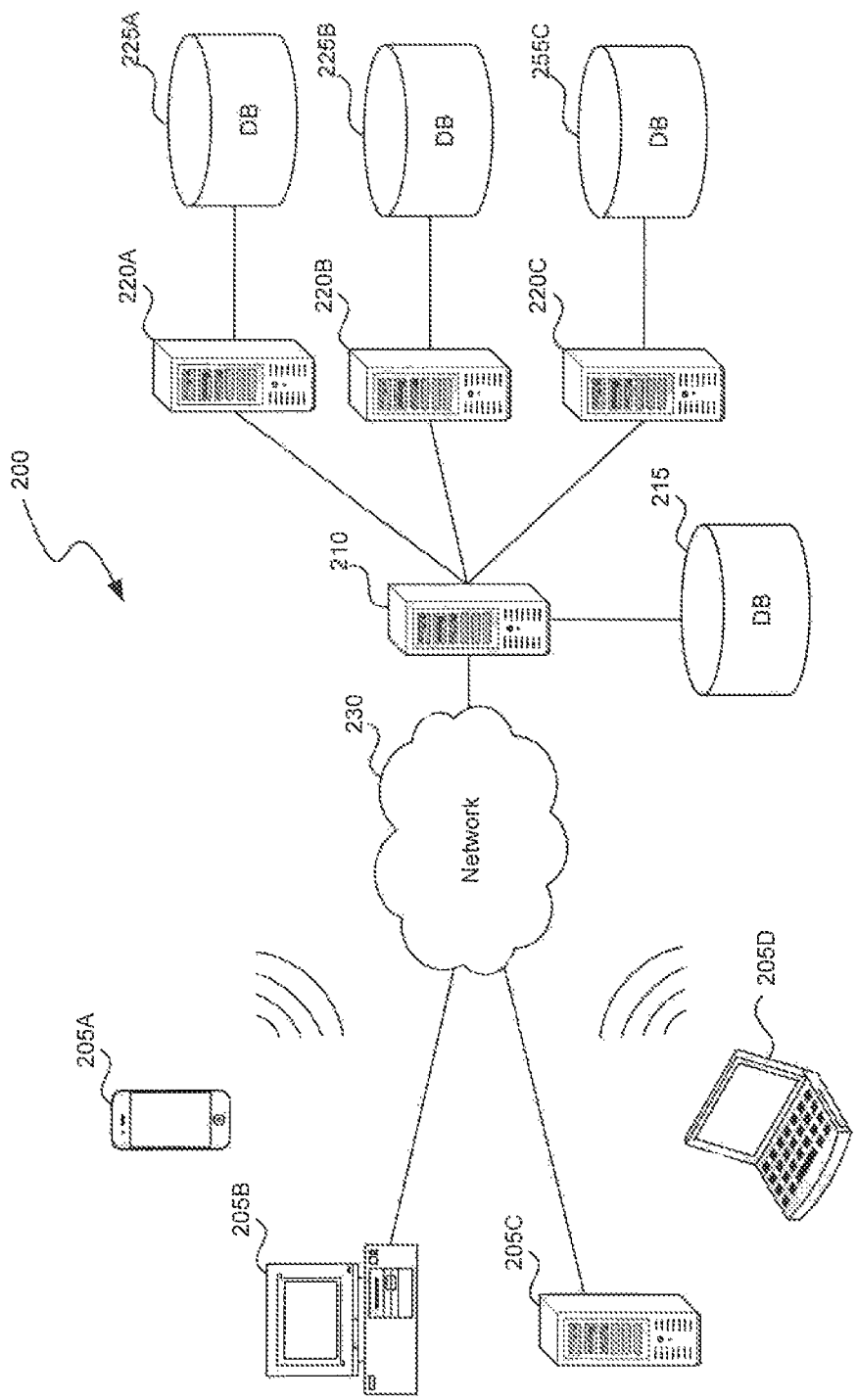
FIG. 2 is a block diagram illustrating an overview of an environment in which some implementations of the present technology can operate.

FIG. 2 is a block diagram illustrating an overview of an environment 200 in which some implementations of the disclosed technology can operate. Environment 200 can include one or more client computing devices 205A-D, examples of which can include device 100. Client computing devices 205 can operate in a networked environment using logical connections 210 through network 230 to one or more remote computers, such as a server computing device.

In some implementations, server 210 can be an edge server which receives client requests and coordinates fulfillment of those requests through other servers, such as servers 220A-C. Server computing devices 210 and 220 can comprise computing systems, such as device 100. Though each server computing device 210 and 220 is displayed logically as a single server, server computing devices can each be a distributed computing environment encompassing multiple computing devices located at the sense or at geographically disparate physical locations. In some implementations, each server 220 corresponds to a group of servers.

Client computing devices 205 and server computing devices 210 and 220 can each act as a server or client to other server/client devices. Server 210 can connect to a database 215. Servers 220A-C can each connect to a corresponding database 225A-C. As discussed above, each server 220 can correspond to a group of servers, and each of these servers can share a database or can have their own database. Databases 215 and 225 can warehouse (e.g., store) information such as medication circadian profiles, observed changes in circadian rhythms from using particular medications, observed patient results in circadian rhythm adjustments from using light therapy, observed circadian rhythm disruptions for medication combinations, prescribed medication regimens, API data for the circadian rhythm entrainment platform or for third-party systems, etc. Though databases 215 and 225 are displayed logically as single units, databases 215 and 225 can each be a distributed computing environment encompassing multiple computing devices, can be located within their corresponding server, or can be located at the same or at geographically disparate physical locations.

Network 230 can be a local area network (LAN) or a wide area network (WAN), but ban also be other wired or wireless networks. Network 230 may be the Internet or some other public or private network. Client computing devices 205 can be connected to network 230 through a network interface, such as by wired or wireless communication. While the connections between server 210 and servers 220 are shown as separate connections, these connections can be any kind of local, wide area, wired, or wireless network, including network 230 or a separate public or private network.

Various aspects of a circadian rhythm entrainment platform can exist on different portions of system 200. For example, a patient can access the circadian rhythm entrainment platform using an application, e.g., a mobile app, desktop application, or via a browser application through a website served by one of the server devices. In some implementations, the circadian rhythm entrainment platform can be a stand-alone application, storing patient and application data (e.g., circadian profiles, circadian rhythm adjustment to light therapy mappings, etc.) locally. In some implementations, patient data can be backed-up to remote storage and application data can be updated, either automatically or upon user or administrator request. In other implementations, the circadian rhythm entrainment platform can have client-facing aspects, such as the above application or website and server-facing aspects. Some features of the server-facing aspects can serve data to and store data from the client-facing aspects, such as serving a website or other GUI elements, provide the latest circadian profiles or other mappings, provide remote storage for patient data, etc.

In some implementations, the circadian rhythm entrainment platform can also interface with various third-party entities, either directly by an application on a client device or via a connection through a server-facing aspect. Interfacing with third-party entities can include accessing APIs or otherwise making a call to a web service, sending email or other messages, writing to a database, or interacting with an automated phone system. Examples of third-party entities include medication providers or other research facilities that identify mappings of medications to circadian rhythm disruptions, physician offices, pharmacies, insurance providers, a patient's service for aggregating their medical records, health or fitness tracking services, calendar services, F.D.A., etc. Such interfaces with third-party entities allow the circadian rhythm entrainment platform to keep updated circadian profiles for medications and mappings of circadian rhythm disruptions to light therapy regimens, receive patient medication instructions from medical providers, update medical providers on results of medications, inform medical providers on the effect of a medication on a patient's circadian rhythm, provide treatment verification data to insurance providers, and receive and store data on a patient's history from their medical record aggregation service or health or fitness tracking service. In some implementations, this data can be used to automatically establish a user profile, obtain circadian rhythm data, store treatment statistics and results, etc. Additional features of interactions provided by the circadian rhythm entrainment platform are described below in relation to FIG. 6.

Establishing Medication Circadian Profiles

Figure 3:
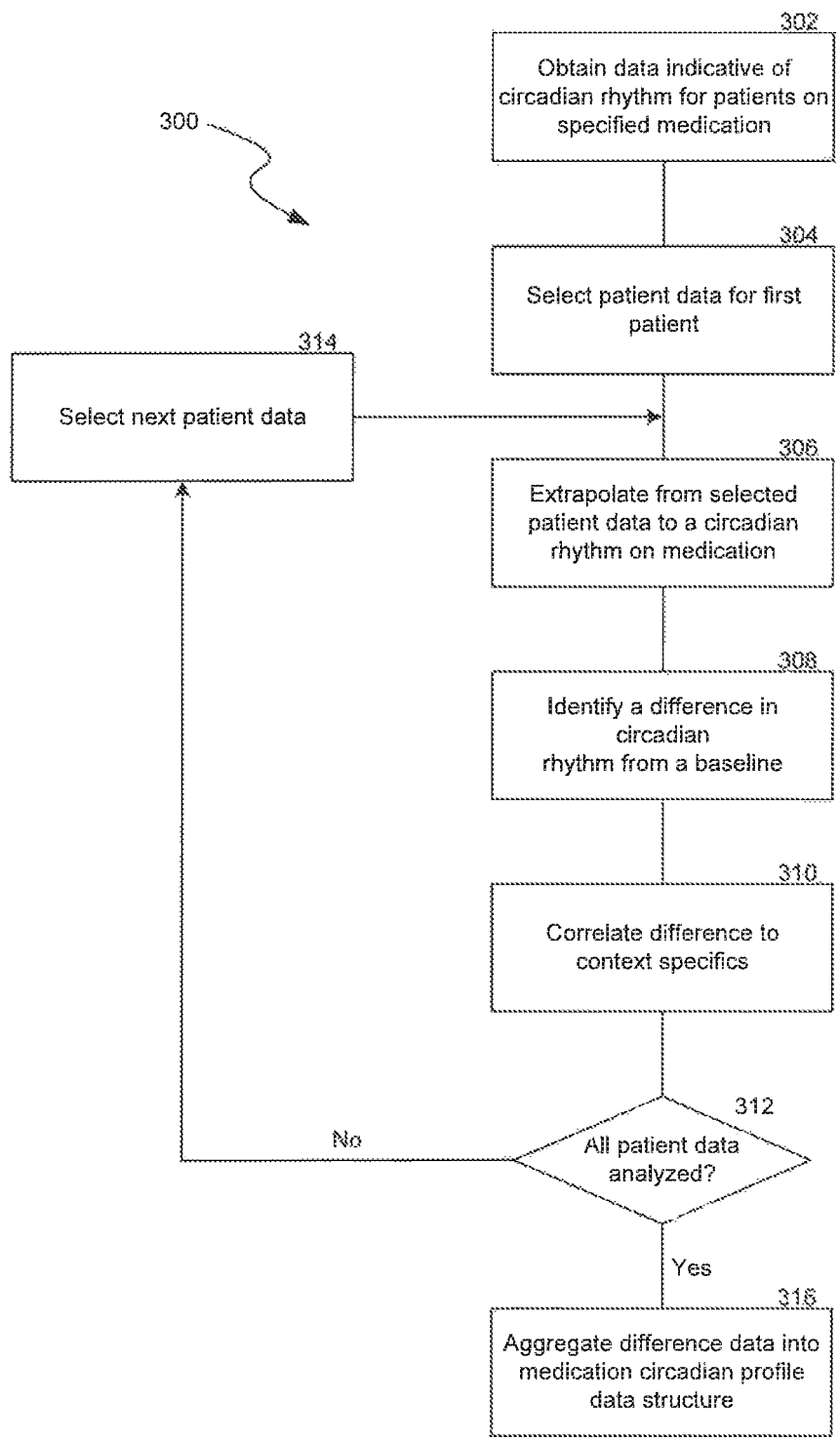
FIG. 3 is a flow diagram illustrating a process used in some implementations of the present technology for establishing medication circadian profiles.

FIG. 3 is a flow diagram illustrating a process 300 used in some implementations for establishing medication circadian profiles. A medication circadian profile or "circadian profile" is a data structure (e.g., data object, entry in a database, file, xml block, or other structured data) comprising identifications of one or more medications and a mapping of the one or more medications to a profiled shift. A "profiled shift" can include one or more of: (a) an expected change in a patient's circadian rhythm, (b) an amount to shift or adjust a patient's circadian rhythm to offset the expected circadian rhythm side effects, or (c) a preferred circadian rhythm state (e.g., an ideal pre-treatment circadian rhythm to offset expected circadian rhythm side effects). Circadian profiles can be used in a circadian rhythm entrainment platform to determine a light therapy regimen to offset side effects of the one or more medications. A circadian profile can be based on observations (e.g., from clinical trials, patient reports in clinical practice, circadian rhythm entrainment platform user feedback, etc.) of changes to circadian rhythms in patients when the patients are taking the one or more medications. Circadian profiles for a medication or combination of medications can be derived from an analysis of the circadian-related side effects such as fatigue or sleep/wake cycle disruption experienced by patients taking the one or more medications.

In some implementations, a circadian profile can specify multiple profiled shifts. For example, a circadian profile can include a pre-treatment amount to modify a circadian rhythm such that, when the medication course is begun, the side effects of the medications are reduced. In a more specific example, it may be known that when patients begin a medication they immediately experience a +2 hour change to the peak melatonin in their circadian rhythm. It may be further determined that a regimen of light therapy can take several days to compensate for this change when on this medication. However, by specifying a pre-treatment profiled shift of −1 hour, the patient is likely to only experience a +1 hour change from a normal circadian rhythm when beginning the medication. This is expected to result in less fatigue and other detrimental symptoms, and the light therapy regimen can more effectively return the patient to a normal circadian rhythm.

In some implementations, the circadian profile can also specify different profiled shift amounts for different stages in medication. For example, a medication can be known to cause a first circadian rhythm change during the first two weeks of treatment and a different circadian rhythm change during the remainder of treatment. The circadian profile can identify different profiled shifts for these stages in medication. In various implementations, a circadian profile data structure can also include other modifiers specifying adjustments to the profiled shifts for particular situations. "Modifiers" can specify either a modification of a baseline profiled shift amount or different profiled shift for different circumstances. Examples of modifiers include modifiers for an amount of medication prescribed, a medication administration schedule, interactions with other medications, patient specifics (e.g., age, gender, lifestyle, occupation or other stressors, etc.), or condition for which the medication was prescribed.

In some implementations, circadian profiles can be used to determine a profiled disruption for a combination of medications. In some implementations, the profiled disruption amount for a combination of medications can be based on observations of circadian rhythm disruptions experienced by patients taking that combination of medications. In other implementations, a profiled disruption amount for a combination of medications can be determined algorithmically, e.g., by combining the profiled disruption amounts for the various medications in the combination. In some implementations, this combination can include applying various weighting factors determined for medications or medications when in combination with certain classes of other medications. For example, a medication can have a profiled shift amount of +3.5 hours, but can be observed to have only half the circadian rhythm effect when used in combination with other medications that have at least a +2 hour shift. Thus, a weighting factor of 0.5 can be applied to the profiled shift for the medication when it is used in combination with other medications with a profiled shift of at least +2 hours.

In some implementations, the weighting factor can be based on a type or class of the other medications. As examples, a medication can be determined to have a +1 hour greater circadian rhythm effect or a 1.5 times less circadian rhythm effect when used in combination with a particular type of drug. Thus, such a weighting factor can be applied when the medication is used in combination with that type of drug.

In various implementations, medication circadian profiles can be generated by drug manufacturers or other researchers, by a regulatory body (e.g., the U.S. Federal Drug Administration (F.D.A.)), by a circadian rhythm entrainment platform based on user data, or by a combination thereof. For example, an initial circadian profile can be generated by a manufacturer of a particular medication/drug, and the initial circadian profile can be updated by a circadian rhythm entrainment platform based on additional data regarding how such medications (as reported by users of the circadian rhythm entrainment platform) affect their circadian rhythms.

There is a wide range of medications the use of which can be improved by combining use with a light therapy regimen. Examples of such, medications include, among others, anti-cancer medications, anti-depressant and other neurological medications, medications for circadian sleep disorders, insomnia, medications for cardiovascular disease, blood pressure medications, and/or medications to treat substance abuse.

Continuing with FIG. 3 at block 302, process 300 can obtain data indicative of circadian rhythms for patients on one or more specified medications. In various implementations, this data can come from trial data (e.g., sleep journals, participants' identification of side effects, measured circadian rhythms), patient reports via medical providers, or data provided by users of a circadian rhythm entrainment platform who specify their medications and measure a circadian rhythm. In some implementations, circadian rhythm data such as sleep journals is present in existing data from previous trials/studies, and thus new trials/studies are not needed to determine a circadian profile for the medication(s).

At block 304, process 300 can select the data for a first patient. At block 306, process 300 can extrapolate, from the selected patient data, one or more circadian rhythms for the patient while on the medication. The extrapolation can include plotting melatonin readings, identifying an expected circadian rhythm based on recorded sleep or other activity, determining a circadian rhythm based on patient identifications of sleep side effects (e.g., from a clinical trial/study or medical provider records). In some implementations, the extrapolation can be performed using a trained model or other statistical analysis generated from data where patients' circadian rhythms and sleep activity or patient data are known.

At block 308, process 300 can identify one or more shifts in the patient's circadian rhythm. Where the selected patient data includes data sufficient to determine the patient's circadian rhythms at various stages of the course of medication, such as before the patient started the medication and at one or more points during the course of treatment using the medication, the identified shifts can be differences between these circadian rhythms. Where only a circadian rhythm can be identified for the patient while on the medication, the shift can be a difference between the patient's circadian rhythm and a normal circadian rhythm.

At block 310, process 300 can correlate the identified shift to context specifics. This can include correlations to other medications the patient is taking concurrently or to any of the contexts for modifiers (e.g., patient age or gender, amount of medication taken, medication schedule, etc.) discussed above.

At block 312, process 300 can determine whether all the patient data obtained at block 302 has been analyzed by the process between blocks 306-314. If not, process 300 returns to block 314 where patient data for a next patient is selected for analysis by the process between blocks 306-314. If so, process 300 continues to block 316.

At block 316, process 300 can aggregate the identified disruptions from multiple instances of block 308 into a circadian profile data structure for the specified one or more medications. The aggregation can include averaging or otherwise combining the identified disruptions into an overall "profiled shift" for the specified medications. In some implementations, the identified disruptions can be grouped according to medication stage and a shift profile can be identified for each stage. In some implementations, some of the stages can be based on similarities of patient circadian rhythms while on the medication. For example, it can be identified that most patients experience a significant circadian rhythm change after four days on the specified medication, thus a stage can be established from beginning the medication to four days.

In some implementations, the aggregation can also include aggregating the context specifics identified at block 310 and incorporating those as modifiers for the profiled shifts, e.g., by identifying different shifts for patient data with the same correlated context elements.

The generated circadian profiles can be stored as a data structure indexed by medication identifier and specifying one or more expected alterations the medication is expected to have on a patient's circadian rhythm. The data structures can be applicable as input for an algorithm (discussed below in relation to FIG. 5) that can convert the mapping to a prescribed regimen of light therapy to prevent or correct disruptions of the patient's circadian rhythm from a normal cycle (referred to herein as "normalizing" the patient's circadian rhythm). In some implementations, input to the algorithm can also include an identification of the patient's current circadian rhythm.

Determining a Current Circadian Rhythm

Figure 4:
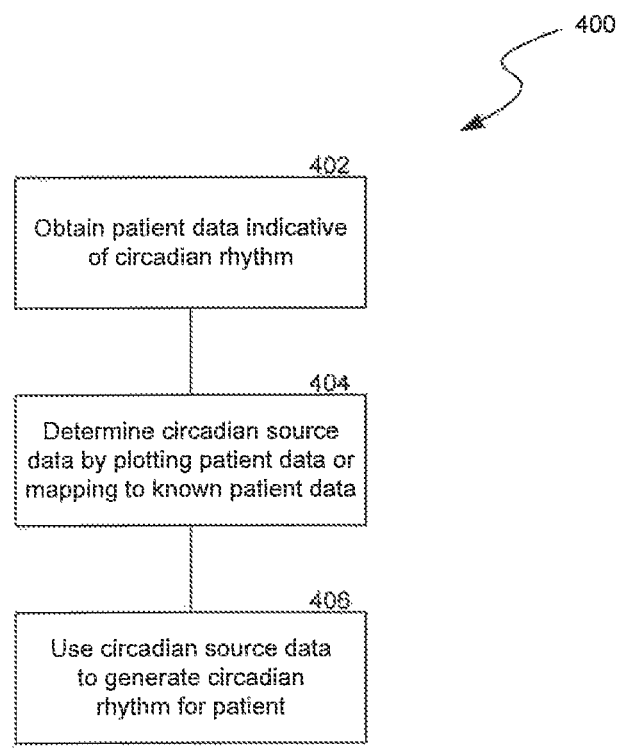
FIG. 4 is a flow diagram illustrating a process used in some implementations of the present technology for determining a patient's current circadian rhythm.

FIG. 4 is a flow diagram illustrating a process 400 used in some implementations for determining a patient's current circadian rhythm. At block 402, process 400 can obtain patient data indicative of a circadian rhythm. In some implementations, this data can include measurements of the patient's melatonin at various points in a time period. For example, melatonin measurements can be taken every 2-3 hours over a 24-72 hour period. Such measurements can be taken by a melatonin assay, e.g., using blood, urine, or saliva. In some implementations, the patient data can be indications of the patient's activity (e.g., sleep activity, level of movement, etc.), gathered by a mobile phone, fitness tracker, or other wearable device or sensor, taken over a time period. In some implementations, the melatonin assay or activity tracking can be performed by a user device, which may be able to connect with a patient's mobile device or a network to provide readings to the circadian rhythm entrainment platform. In some implementations, the patient data can be user-entered data, such as responses to questions or a sleep log (e.g., when the patient falls asleep and wakes up, sleep interruptions, restfulness of sleep, etc.).

At block 404, process 400 can determine circadian source data by plotting the received patient data or by mapping elements of the received patient data to existing patient data that includes a known circadian rhythm. Process 400 can plot the patient data when the patient data includes indications of melatonin levels of the patient at particular times, e.g., from assay data. Process 400 can map the patient data to a known circadian rhythm when the patient data does not include melatonin measurements. In some implementations, this mapping can include one or more of: finding a closest match between the available patient data and patient data with a known circadian rhythm and using the known circadian rhythm. In other implementations, this mapping can include applying a machine learning model trained on training items, each training item including various features of patient data as input and a known circadian rhythm as output.

At block 406, process 400 can use the circadian source from block 404 to generate a circadian rhythm for the patient. For example, process 400 can connect plotted melatonin measurements or fit them to a function, can convert model output to a circadian rhythm graph, or can use machine learning model output or a matched known circadian rhythm. In some implementations, the generated circadian rhythm can be stored in association with the patient in the circadian rhythm entrainment platform.

Determining Light Therapy Regimens in Relation to Medications

Figure 5:
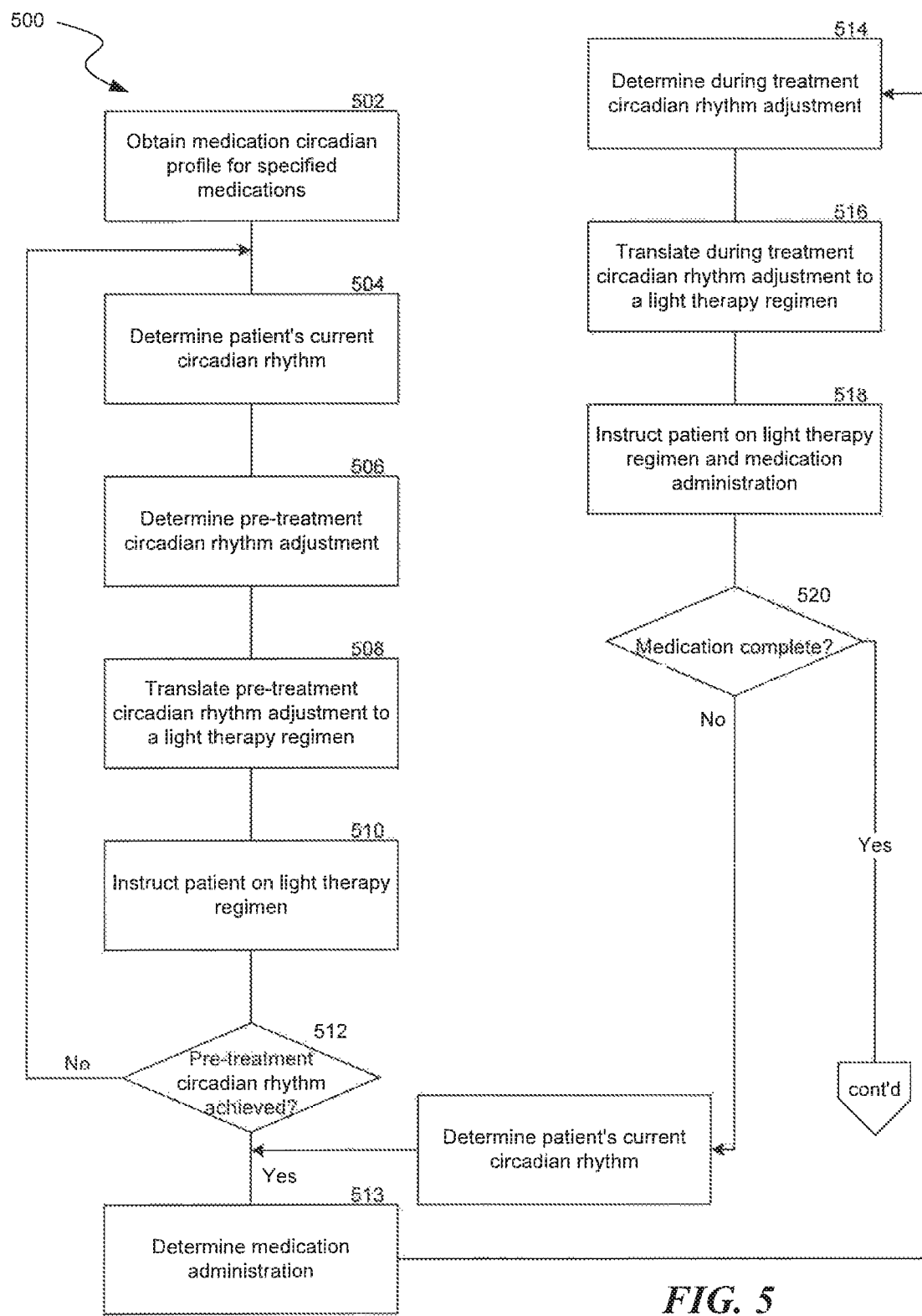
FIG. 5 is a flow diagram illustrating a process used in some implementations of the present technology for determining light therapy regimens before, during, and after a course of medication.
Figure 5:
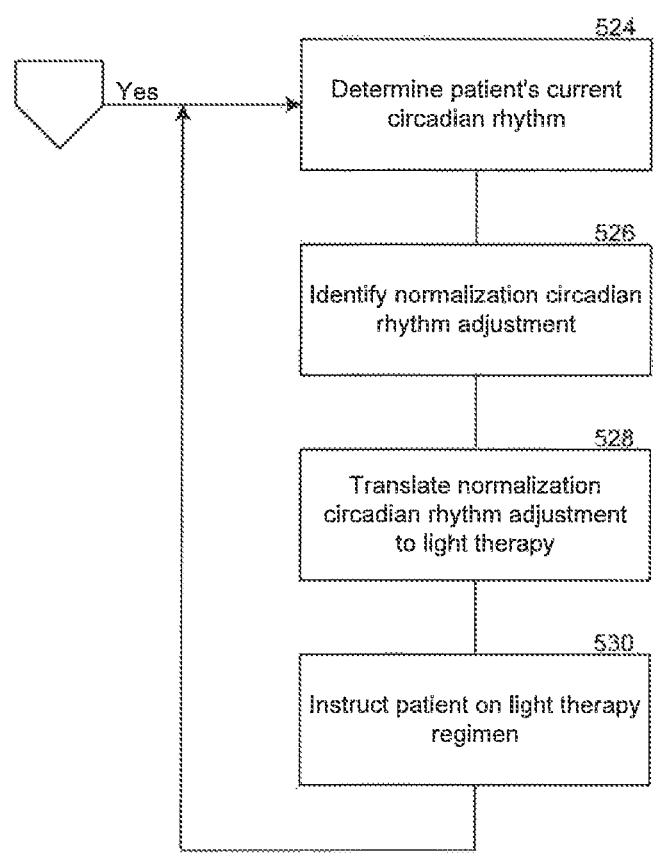

FIG. 5 is a flow diagram illustrating a process 500 used in some implementations for determining light therapy regimen before, during, and after a course of medication. A patient's circadian rhythm is regulated by a variety of factors including exposure to light and dark. The range of visible light is 400 nm (violet) to 700 nm (red). Visible light impacts and helps to regulate circadian rhythm by signaling the brain via non-visual photoreceptors on the retina called "melanopsin." Melanopsin is known to be key to regulating the circadian rhythm because it is highly sensitive to specific wavelengths of light in the blue (and to a lesser extent, green) portion of the visible spectrum (460 nm-550 nm), which are also the peak wavelengths of sunlight. When melanopsin receptors are stimulated by photons of light in this wavelength range, the receptors interpret the light as the 'day' period and, in what is thought to be a primordial 'survival instinct', send a signal via the optic nerve to the SCN in the brain that it needs to be 'alert'. This in turn triggers a cascade of reactions across several rhythms in the body including suppression of the 'sleep' hormone melatonin.

Various light therapy devices mimic these blue and green wavelengths for maximum photonic response by a patient's melanopsin receptors. In addition, various apparatus such as specialized glasses can block light in these wavelengths minimizing photonic response by a patient's melanopsin receptors. Alternatively, a patient can simply avoid light in these wavelengths, Controlling the timing and duration of these maximum and minimum light-exposure periods (a "light therapy regimen") can adjust a patient's circadian rhythm. Process 500 illustrates how a circadian rhythm entrainment platform can determine a light therapy regimen that will prevent or compensate for side effects resulting from various medications. Process 500 can also help determine when to administer medications based on the patient's circadian rhythm to increase effectiveness.

Process 500 begins at block 502 by obtaining one or more circadian profiles for a specified one or more medications a patient is taking or plans to take. In some implementations, the obtained circadian profiles can be data structures generated by process 300. As discussed above, in various implementations, circadian profiles can include a single profiled disruption for a medication or can include multiple profiled disruptions for different stages of medication. In some implementations, process 500 can obtain the circadian profiles from a repository of the circadian rhythm entrainment platform or by interfacing with an external source, such as a medication provider. In some implementations, process 500 can receive an identification of the specified one or more medications from input by the patient or by interfacing with a doctor's office or other medical system.

At block 504, process 500 can determine a patient's current circadian rhythm. In some implementations, process 400 (FIG. 4) can be applied to determine the patient's current circadian rhythm. In some implementations where patient circadian rhythm data is not available, process 500 can assume a normal starting circadian rhythm for the patient.

In some implementations, process 500 includes blocks 506-512 to pre-compensate for expected circadian rhythm changes due to medication(s), prior to starting the medication(s). However, in other implementations, process 500 skips block 506-512, going to block 513, starting light therapy in conjunction with starting the specified one or more medications.

At block 506, process 500 can determine a pm-treatment circadian rhythm adjustment to apply to the patient's circadian rhythm through light therapy, prior to beginning medication. In some implementations, the pre-treatment circadian rhythm adjustment can be the difference between the determined patient's circadian rhythm from block 504 and a normal circadian rhythm, to bring the patient to a normal circadian rhythm prior to starting medication. In some implementations, the pre-treatment circadian rhythm adjustment can be a difference between the determined patient's circadian rhythm from block 504 and a pre-treatment optimal circadian rhythm. A pm-treatment optimal circadian rhythm can be an amount away from a normal circadian rhythm the patient's circadian rhythm should be to minimize the side effects expected from starting the medication. In some implementations, the pre-treatment optimal circadian rhythm can be specified in the circadian profile for the specified one or more medications or can be computed based on an expected initial circadian rhythm change caused by the medications. In some implementations, the pre-treatment optimal circadian rhythm can be based on patient specifics (e.g., different pre-treatment optimal circadian rhythms for different aged patients) or medication specifics (e.g., different pre-treatment optimal circadian rhythms for different medication amounts or administration plans).

At block 508, process 500 can translate the pre-treatment circadian rhythm adjustment determined at block 506 into a light therapy regimen, or if a previous light therapy regimen has been provided, to an updated light therapy regimen. Translating a circadian rhythm adjustment into a light therapy regimen can be based on specifics and effectiveness of the light therapy system being applied. The circadian rhythm entrainment platform can access functions that receive a circadian rhythm adjustment and produce a suggested light therapy regimen for a particular light therapy system. In some implementations, the functions can further receive patient specifics (e.g., age, gender, etc.) and produce a suggested light therapy regimen for a particular light therapy system for patients with those characteristics. In some implementations, the functions can be based on observed results of various patients (or patients with the specified characteristics) using the light therapy systems. For example, it can be observed that applying light therapy for 15-30 minutes immediately before the peak melatonin in the patient's circadian rhythm tends to shift that peak later and applying a similar light therapy treatment after the peak melatonin tends to shift that peak earlier.

In some implementations, the circadian rhythm entrainment platform can track a patient's compliance with a light therapy regimen, either via communication with a light therapy device, or by receiving input from the patient specifying that he/she completed the prescribed light therapy. In some implementations, an updated light therapy regimen can be based on a patient's previous light therapy compliance, adjusting the light therapy to compensate for missed light therapy sessions.

At block 510, process 500 can cause an indication of the light therapy regimen determined at block 508 to be conveyed via a device associated with the patient. In some implementations, for example, the determined light therapy regimen can specify parameters for light therapy, such as durations and times of use, and at block 510 these parameters can be used to select or populate light therapy instruction templates. In some implementations, the device associated with the patient can be the patient's mobile device, which can provide instructions for using a light therapy system. In some implementations, the device associated with the patient can be the light therapy device, which can be automatically configured to provide the determined light therapy regimen. In some implementations, the circadian rhythm entrainment platform can provide various messaging and reminders to the patient for their light therapy. Such notifications can be provided, for example, through a mobile device application, though a desktop application, by interfacing with a calendar or other third-party alert system, by sending email or other messages, etc. The circadian rhythm entrainment platform can also provide reminders and other messaging, e.g., for taking medication, for measuring melatonin levels, etc.

In some implementations, blocks 506-512 are performed only once to determine a prescribed pre-treatment light therapy regimen, which the patient then follows to correct for expected medication effects on their circadian rhythm. In other implementations, blocks 506-512 can be repeated periodically to determine an updated light therapy regimen, e.g., to account for differences in how the patient's circadian rhythm is actually responding to the light therapy regimen. Where blocks 506-512 are repeated, this portion of process 500 can be repeated on a periodic schedule, when new data is obtained (e.g., when a new circadian rhythm measurement for the patient can be taken or when new circadian profiles for the one or more medications are obtained), or in response to a patient trigger (e.g., the patient requesting an updated light therapy regimen through the circadian rhythm entrainment platform). Where blocks 506-512 may be performed more than once, at block 512, process 500 can determine whether a pre-treatment circadian rhythm has been achieved. In some implementations, this can be based on a measurement of the patient's circadian rhythm being within a threshold amount of normal or the pre-treatment optimal circadian rhythm. In some implementations, this can be based on an indication that the patient has completed the pre-treatment light therapy regimen, which was expected to bring the patients circadian rhythm close to normal or the pre-treatment optimal circadian rhythm. If the pre-treatment circadian rhythm has not been achieved, process 500 can return to block 504. If the pre-treatment circadian rhythm has been achieved, process 500 can continue to block 513.

At block 513, process 500 can determine a medication administration schedule for the selected medications. In some implementations, medications can have circadian effectiveness levels where the medications are determined to be more effective at particular points in a patient's circadian rhythm. For example, based on patient feedback in clinical trials, a medication can be determined to be most effective immediately after the melatonin peak in a circadian rhythm. This can be determined based on clinical trials, patient feedback in clinical practice, etc. The circadian profiles for the medications can include this information. Process 500 can have an expected circadian rhythm for the patient, either based on measured melatonin or activity or based on the pre-treatment light therapy regimen. Process 500 can determine a schedule for medication administration where the medications will be most effective, according to the expected patient circadian rhythm and the medication circadian effectiveness levels. Process 500 can cause the medication administration schedule to be conveyed via a device associated with the patient, e.g., using templates. In some implementations, process 500 can skip setting a medication administration schedule, such as where such a schedule has been dictated by a medical provider.

At block 514, process 500 can determine a during-treatment circadian rhythm adjustment to apply to the patient's circadian rhythm through light therapy during a course of the specified one or more medications. In some implementations, the during-treatment circadian rhythm adjustment can be the difference between a normal circadian rhythm and either the pre-treatment circadian rhythm from block 512 or the determined patient's circadian rhythm from block 522. This is referred to as the reactive light therapy application, where the light therapy regimen is applied to compensate for effects of the medication that have already occurred, in an attempt to return the patient's circadian rhythm to normal. In some implementations, the during-treatment circadian rhythm adjustment can be an adjustment determined by computing an uncompensated circadian rhythm that will result from applying the profiled adjustment (from the circadian profiles for the one or more medications) to the patient's expected circadian rhythm (either measured at block 522 or 512 or is the pre-treatment optimal) and then determining a difference between the uncompensated circadian rhythm and a normal circadian rhythm. This is referred to as the predictive light therapy application, where the circadian rhythm entrainment platform identifies how the specified one or more medications are expected to affect the patient and proactively determining a therapy needed to adjust for expected future circadian rhythm changes. Thus, the light therapy regimen is applied to pre-compensate for effects of the medication that are expected to occur, in an attempt to keep the patient's circadian rhythm at normal despite effects of the medication.

In some implementations where the circadian profiles include different profiled disruptions for different stages of the medication or have modifiers of the disruption for different circumstances, the uncompensated circadian rhythm can be computed for the current stage in the course of the medication or for other context specifics of the patient matching the modifiers. The current medication stage and other context specifics can be tracked by the circadian rhythm entrainment platform or can be entered by the patient.

At block 516, process 500 can translate the during-treatment circadian rhythm adjustment determined at block 514 into a light therapy regimen. Similarly to block 508, this can be based on specifics and effectiveness of the light therapy system being applied. Also similarly to block 508, the circadian rhythm entrainment platform can perform this translation by applying functions that receive a circadian rhythm adjustment and produce a suggested light therapy regimen for a particular light therapy system, which can include durations and levels of light exposure, and durations to avoid light or light in particular bandwidths. The circadian rhythm entrainment platform can interface with a light therapy device to receive records of treatment or can receive records of light therapy treatment entered by the patient. If the patient skipped or incorrectly applied a light therapy session, the translation process can adjust the light therapy regimen to account for the missed session.

At block 518, process 500 can cause an indication of the light therapy regimen determined at block 516 to be conveyed via a device associated with the patient. This can be performed in a manner similar to block 510.

In some implementations, blocks 513-518 are performed only once to determine a prescribed light therapy regimen, which the patient then follows to correct for expected medication effects on their circadian rhythm. In other implementations, blocks 513-522 can be repeated periodically to determine an updated light therapy regimen, e.g., to account for differences in how the patient's circadian rhythm is actually responding to the medication and/or the light therapy regimen or to determine an updated light therapy regimen for different stages in the course of the medication. Where blocks 513-522 can be repeated, triggering this portion of process 500 can be from a periodic schedule, based on an identification of a next medication stage, when new data is obtained (e.g., when a new circadian rhythm measurement for the patient can be taken or when new circadian profiles for the one or more medications are obtained), or in response to a patient trigger (e.g., the patient requesting an updated light therapy regimen through the circadian rhythm entrainment platform). Blocks 513-522 can be repeated until the course of medication is complete. If the course of medication is not complete, process 500 can proceed to block 522 upon the trigger. At block 522, process 500 can determine the patient's current circadian rhythm, e.g., using process 400. Process 500 can then return to block 513.

In some implementations, process 500 ends after block 518 or block 520. In other implementations, blocks 524-530 can be performed following the course of medication to return and keep the patient's circadian rhythm to normal. At block 524, process 500 can determine the patient's current circadian rhythm, e.g., using process 400 (FIG. 4). At block 526, process 500 can identify a normalization circadian rhythm adjustment. The normalization circadian rhythm adjustment can be a difference between the patient's current circadian rhythm and a normal circadian rhythm. At block 528, process 500 can translate the normalization circadian rhythm adjustment into a light therapy regimen, which can be performed in a manner similar to block 508. At block 530, process 500 can cause an indication of the light therapy regimen determined at block 528 to be conveyed via a device associated with the patient, which can be performed in a manner similar to block 510. Process 500 can repeat blocks 524-530 at various intervals, e.g., on a periodic schedule, when new data is obtained (e.g., when a new circadian measurement for the patient can be taken), or in response to a patient trigger (e.g., the patient requesting an updated light therapy regimen through the circadian rhythm entrainment platform).

Circadian Rhythm Entrainment Platform Communications and Interfaces

Figure 6:
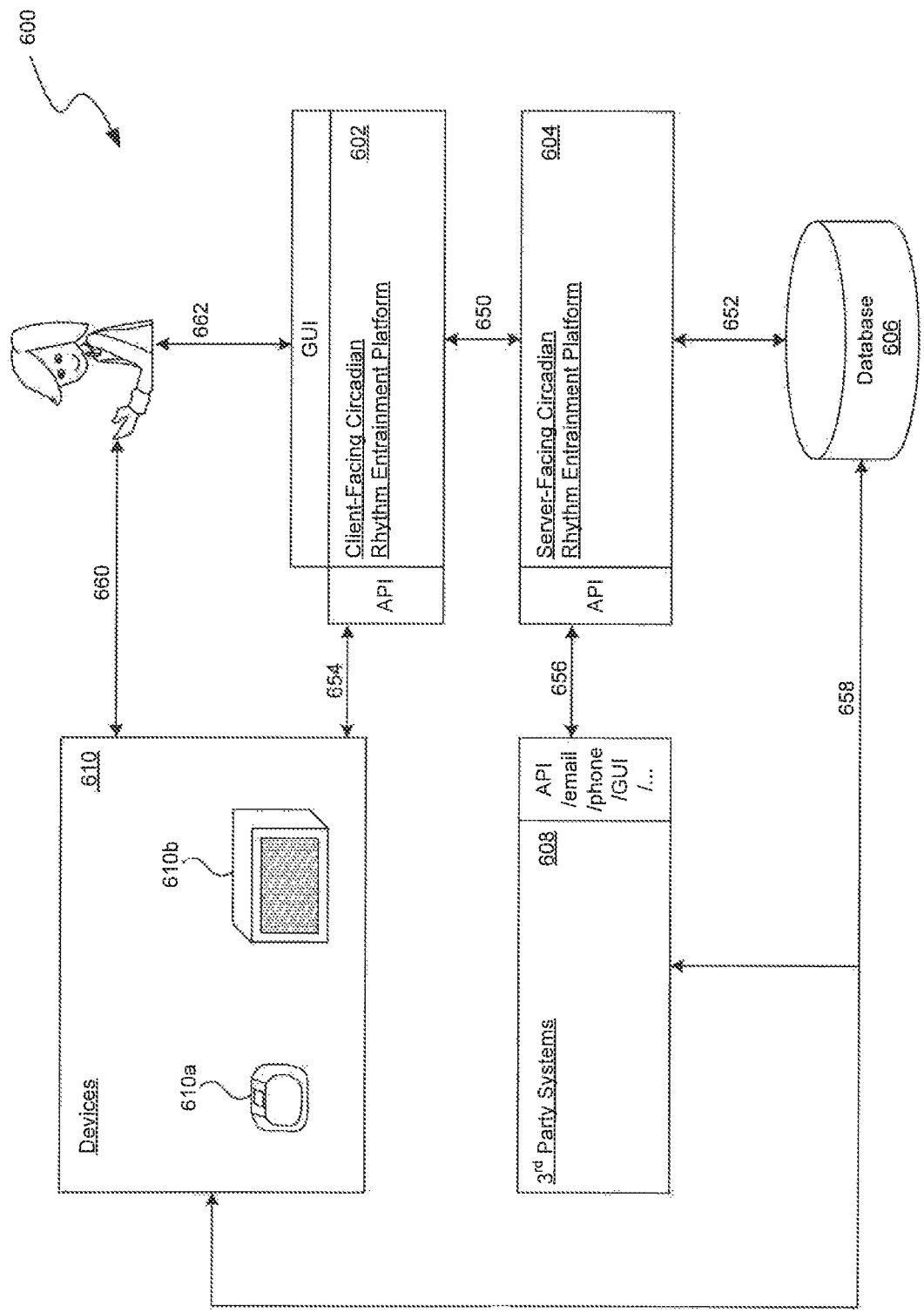
FIG. 6 is a system diagram illustrating example communications and interfaces used in some implementations of a circadian rhythm entrainment platform configured in accordance with the present technology.

FIG. 6 is a system diagram 600 illustrating example communications and interfaces used in some implementations of a circadian rhythm entrainment platform configured in accordance with the present technology. Diagram 600 includes a patient, a client-facing portion of a circadian rhythm entrainment platform 602, a server-facing portion of a circadian rhythm entrainment platform 604, a database 606, third-party systems 608, and devices 610.

The client-facing portion of a circadian rhythm entrainment platform 602 (the "client-facing portion 602") can be a mobile application, a desktop application, or a web interface. In some implementations, client-facing portion 602 can perform any of processes 300-500 described above with reference to FIGS. 3-5, which can be implemented e.g., by one of devices 205, 210, or 220. Data for use by the client-facing portion 602, such as the web interface, circadian profiles (if process 500 is performed client-side, though it can also be performed server-side), light therapy instructions, circadian rhythm entrainment platform updates, etc., can be served at step 650 by server-facing portion 604, or can be obtained directly from other systems such as database 606 or third-party systems 608. Communication at step 650 can be performed over the Internet, Wi-Fi, a cellular network, or via other wired or wireless channels. The client-facing portion 602 can provide one or more APIs for receiving data from other systems, such as devices 610, e.g., at step 654. In various implementations, communications at step 654 can be performed using various connections, such as through Bluetooth, wired connections, over Wi-Fi or another network, etc. The client-facing portion 602 can provide a GUI (e.g., GUI 700) to provide information to the patient and to receive input from the patient, e.g., at step 662. The client-facing portion 602 can also provide various notifications and communications for the patient, such as through mobile device notifications, in-app notifications, messages, etc.

The server-facing portion of a circadian rhythm entrainment platform 604 can be software executed by a system of one or more dedicated or as-needed servers. Server-facing portion 604 can provide support for the client-facing portion 502 (at step 650) and can coordinate communication and provide interfaces between other elements such as database 606 and third-party systems 608 (e.g., at steps 652 and 656). Communications at steps 550, 656, and 652 can be via network communications, e.g., over the Internet. In some implementations, e.g., where the client-facing portion is a stand-alone application, the functionality of the server-facing portion 604 can be provided by the client-facing portion 602. In some implementations, server-facing portion 604 can perform any of processes 300-500, which can be implemented e.g., by one of devices 205, 210, or 220. Sever facing portion 604 can include APIs, allowing third-party systems 608 to implement, at step 656, functionality provided by server-facing portion 604. For example, third-party systems can use these APIs to update circadian profiles, provide indications of medication treatment courses, retrieve treatment data for insurance purposes, obtain data correlating medications to circadian rhythm side effects, etc. Server-facing portion 604 can also, at step 656, make call to APIs provided by third-party systems 608, can send messages to third-party systems 608 (e.g., via email, make HTML, FTP or other connections, SMS, etc.), or can automatically interact with other interfaces to third-party systems 608 (e.g., via automated phone systems, GUIs, etc.). For example, server-facing portion 604 can provide data on treatments or patient conditions to medical providers or insurance companies, can access sleep/activity tracker data, can obtain the latest circadian profiles from medication providers, etc.

In some examples, patient data (which may be authorized for sharing and/or anonymized) correlating circadian rhythm changes to medications can be provided to researchers or medication providers to be used to create or update medication circadian profiles. In some implementations, the circadian rhythm entrainment platform can generate or update its own circadian profiles for medications, as the circadian rhythm entrainment platform may have more or better data mapping patient circadian rhythms to medications. In addition, the circadian rhythm entrainment platform can maintain records of circadian rhythm changes to indications of how patients are performing light therapy and can use this data to generate improved transformation functions for transforming circadian rhythm shifts to light therapy regimens.

Database 606 (or server-facing portion 604) can warehouse data used by the circadian rhythm entrainment platform, such as circadian profiles, patient data (e.g., measured circadian rhythms, patient medication courses, compliance with medication and light therapy courses, tolerance of medication side effects, records of how patients responded to light therapy, activity data, melatonin readings, etc.), data or functions for translating circadian rhythm shifts to light therapy regimens, templates for instructing patients on light therapy regimens, webpages, media content, etc. Database 606 can be accessible by server facing portion 604 and can be hosted by the same or different servers. In some implementations, database 606 can also be accessible (either directly or through server-facing portion 604) by one or more of client-facing portion 602 (not shown), third-patty systems 608, or devices 610. Access to database 606 can be by various network connections or, if the access is by the server-facing portions and the database 606 is local to the server-facing portions 604, by a BUS or other local data transfer mechanism.

Third-party systems 608 can include a variety of entities such as medication providers, research groups, government entities, insurance providers, medical providers, pharmacies, technology companies (e.g., that store sleep and/or fitness tracker data or patient medical records), etc. As discussed above, third-party systems 608 can interface at step 656 with server-facing portions 604, e.g., via APIs. Third-party systems 608 can also communicate with the circadian rhythm entrainment platform through database 606, e.g., when the third-party systems are given appropriate access and write to or read from database 606, at step 658. In some implementations, third-party systems 608 can communicate with devices 610, e.g., where the third-party system manages data from a sleep/activity tracker device, e.g., device 610A. Patients can also directly interact with the third-party systems (not shown).

Devices 610 can include devices associated with a patient, such as a fitness or other sleep or activity tracker 610A, a light therapy device 610B (eg., Litebook® EDGE), or a melatonin assay device (not shown). At step 660, patients can interact with these devices or the devices can monitor aspects of the patients. At step 654, these devices can communicate with the circadian rhythm entrainment platform, e.g., via the patent's mobile device. At step 658, the devices 610 can communicate with a third-party system, database 606, or server-facing portions 604 (not shown). These communications can be via the Internet, Wi-Fi, or a connection to a mobile device (e.g., over Bluetooth).

Circadian Rhythm Entrainment Platform Graphical User Interface

Figure 7:
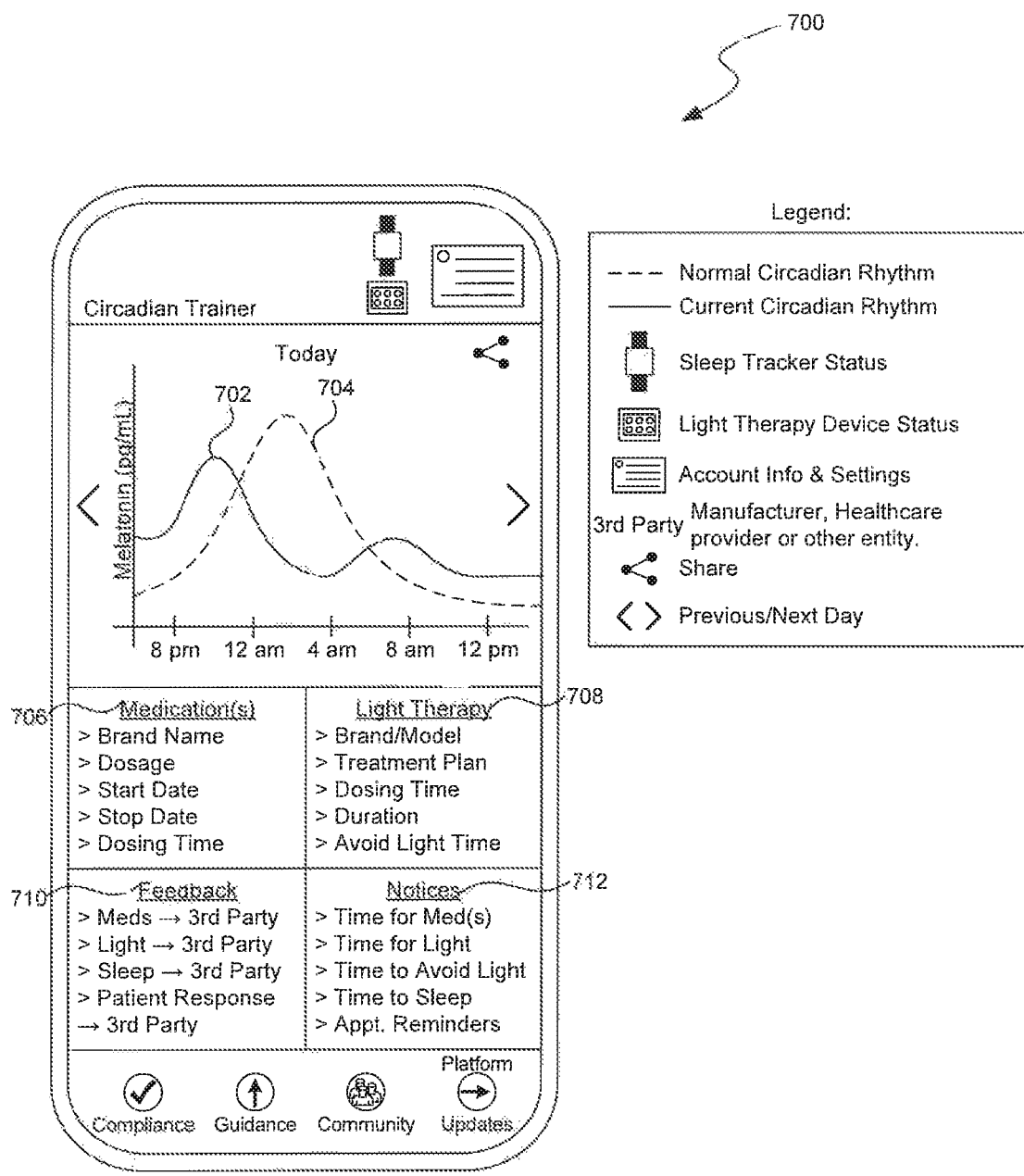
FIG. 7 is a conceptual diagram illustrating an example graphical user interface (GUI) of a client-facing portion of a circadian rhythm entrainment platform.
Figure 8:
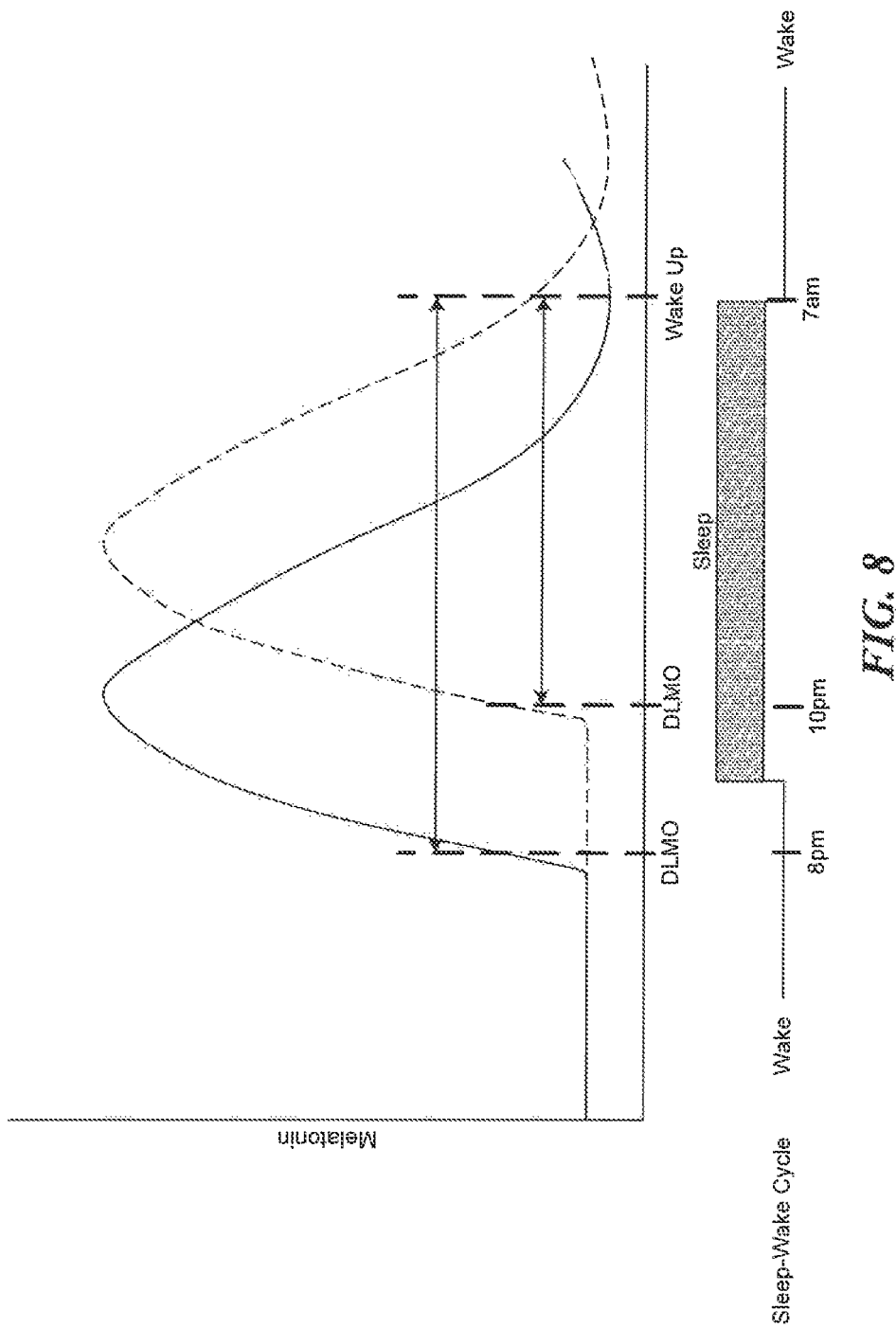
FIG. 8 is a conceptual diagram illustrating an example graphical user interface (GUI) showing a change in a patient's circadian rhythm.

In addition, some implementations of the circadian rhythm entrainment platform can provide various graphics, user interfaces, communication, and notification systems. For example, FIG. 7 is a conceptual diagram illustrating an example graphical user interface (GUI) 700 of a client-facing portion of a circadian rhythm entrainment platform. FIG. 7 illustrates a graphic 700 for displaying a comparison of a patient's current circadian rhythm 702 to a prescribed circadian rhythm 704. In some implementations, the graphics in a circadian rhythm entrainment platform GUI can illustrate how a patient's circadian rhythm has changed, e.g., illustrating multiple curves on different screens by time period or overlapping curves for different circadian rhythms of the patient, indicators of change (e.g., arrows) showing how points on the circadian rhythm have changed, or an animation of how the patient's circadian rhythm has evolved in a given time. Another version of a graphic illustrating a change in a patient's circadian rhythm is provided in FIG. 8.

FIG. 7 also illustrates a number of additional features some implementations of the circadian rhythm entrainment platform can provide, such as a medication list 706 with directions, directions for a light therapy regimen 708, options to provide information to various third parties 710, and notifications 712 (e.g., medication reminders, light therapy reminders, sleep reminders, appointment reminders, etc.). In various implementations, notifications can be provided through notices via an app on a mobile device, by sending messages (e.g., email, SMS, etc.) to the patient, by creating entries in a third-party calendar or to-do list system, etc. The graphical components in FIG. 7 can be shown in a different manner, arranged in different orders, some can be excluded or others included.

Example Changes in a Circadian Rhythm Due to a Light Therapy Regimen

FIGS. 9-13 are conceptual diagrams illustrating an example change in a circadian rhythm due to a light therapy regimen. These figures illustrate particular examples of the 'how' and 'when' for applying bright light and avoiding blue light in a light therapy regimen and the result on circadian rhythms for patients.

FIG. 9, for example, illustrates a "normal" circadian rhythm with an optimized melatonin curve 902 for adults (age 25+), along with curve 904 illustrating cortisol and curve 906 illustrating core body temperature. Area 908 illustrates the patient's sleep period. Though referred to herein as the "normal" circadian rhythm, curve 902 is actually the circadian rhythm that applying light therapy should aspire to achieve, and may not be reflective of any actual circadian rhythms in the public. As is illustrated in FIG. 9, in a normal circadian rhythm, peak melatonin level is approximately 3 am-4 am, normal wake time is 6 am-7 am, DLMO is 9 pm-10 pm, and sleep phase is from 11 pm to 6 am-7 am.

Figure 10:
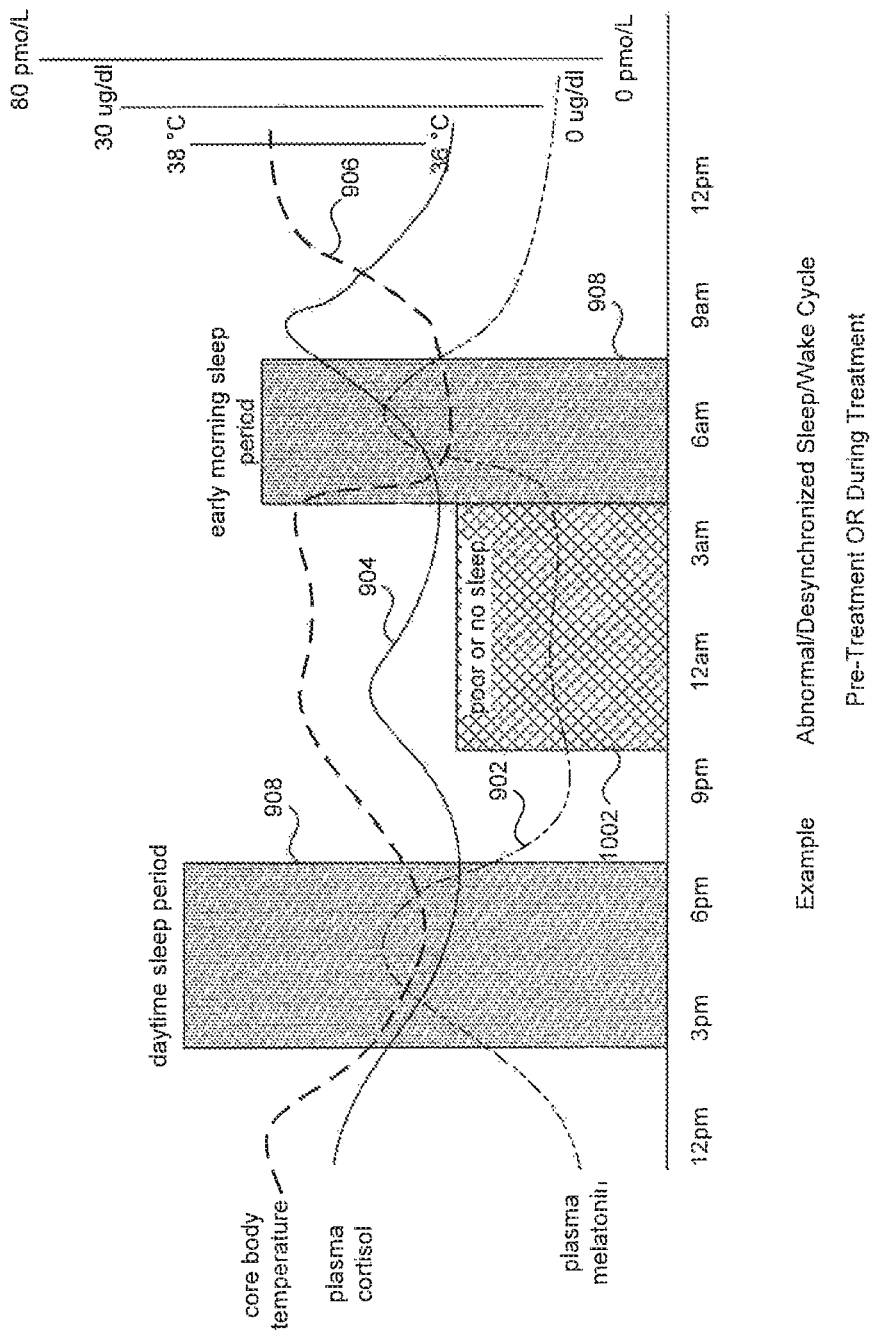

FIG. 10 illustrates data for a patient with an abnormal or disrupted sleep wake cycle. This may be a patient prior to a course of medication with the disruption due to external causes or during the course of medication with the disruption due to the medication(s). The example in FIG. 10 is typical for patients undergoing various cancer treatments, e.g., chemotherapy or radiation. This type of abnormal or disrupted sleep wake/cycle is characterized by: overall poor sleep quality and duration, particularly during the Desired Sleep Period ("DSP") i.e., 11 pm-6 am; frequent daytime sleeps or naps; short sleep periods in early morning (60-90 mins); and serious to severe daytime fatigue. Additional side effects can include low appetite or junk food cravings, poor digestion, constipation, diarrhea, headaches, low mood, irritability, etc. FIG. 10 shows disrupted versions of circadian rhythm melatonin curve 902, cortisol curve 904, and core body temperature curve 906. FIG. 10 also shows versions of sleep periods 908 and a poor or no sleep period 1002.

Figure 11:
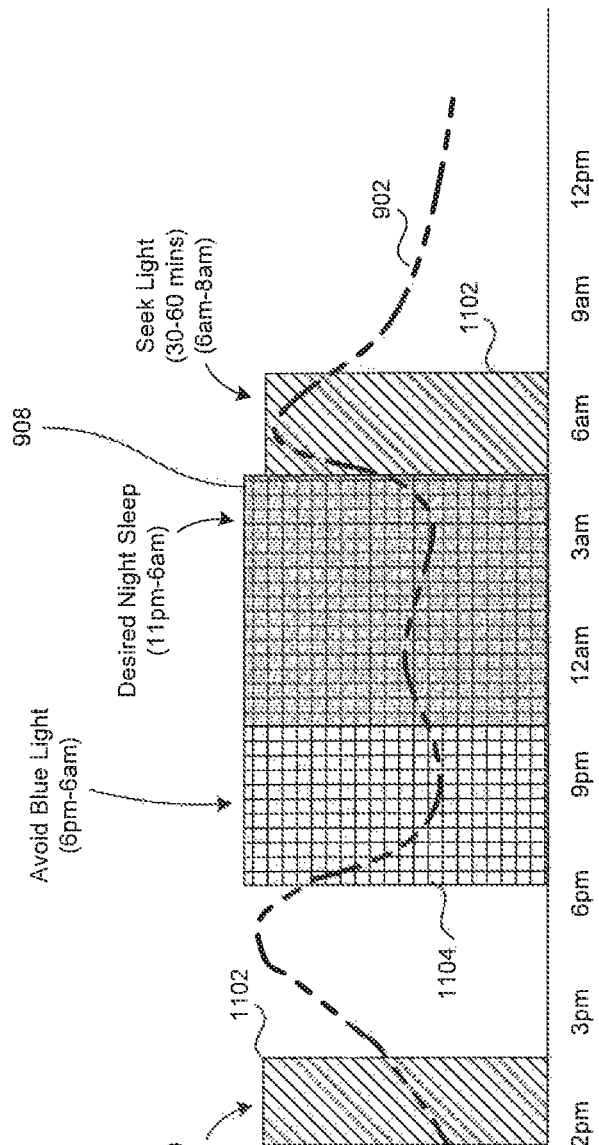
Figure 12:
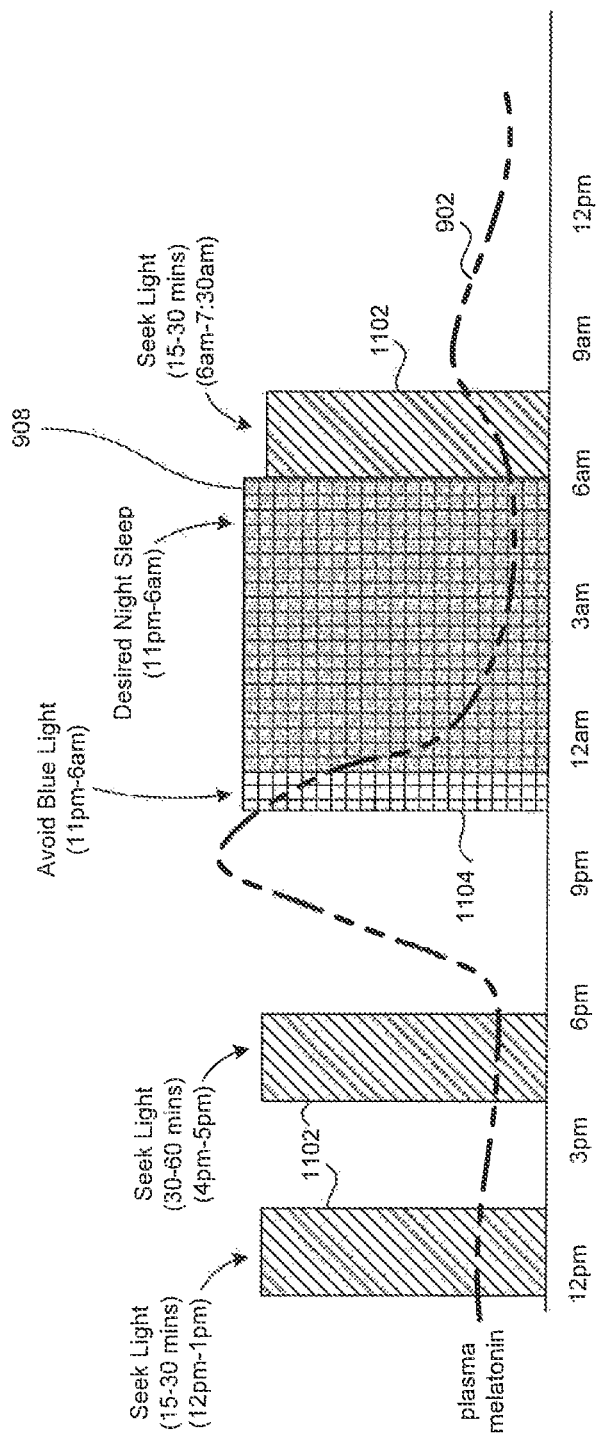

FIGS. 11-13 illustrate the effects of a three-day light treatment regimen where curve 902 illustrates melatonin levels in the patient, areas 908 illustrate desired sleep periods, areas 1102 illustrate times for the patient to seek light therapy (e.g., via a light therapy device), and areas 1104 illustrate times for the patient to avoid light in the blue spectrum (e.g., by avoiding these sources or via glasses that block blue/green light).

For some patients the regimen plan to sync their circadian rhythm will take 1-3 days (or longer, depending on several factors including age, history of circadian disruption, potency of medication, compliance to sync protocol, among others). For the example in FIGS. 11-13, the goal is to adjust the peak melatonin by approximately 10 hours (from the patient's current setting of melatonin peaking at 5 pm in FIG. 11 to 3 am in FIG. 13. This is accomplished in part by using a light therapy device at indicated times 1102 for 30-60 minutes per indicated time frame, which are prior to the patient's current melatonin rise and again at the 'desired' wake time e.g., 6 am-8 am. This is also accomplished by avoiding light in the blue/green spectrums during times 1104, which are following the patient's current melatonin peak and are throughout the evening and night hours, until the desired wake time.

FIG. 11 shows a first stage of a light therapy regimen to normalize a patient's circadian rhythm 902 following no previous light therapy, for example prior to beginning medication, after a course of mediation, or in the reactive application of during-treatment light therapy. In the predictive version of during-treatment light therapy, instead of using the patient's actual circadian rhythm curve 902, a curve modified by the expected amount of shift from taking the medication can be used (i.e., the uncompensated circadian rhythm).

FIG. 12 shows a second stage of a light therapy regimen where the portion of the light therapy regimen from FIG. 11 has started to adjust the melatonin peak of the patient's circadian rhythm 902 later (now at 9 pm). An updated regimen of light therapy is begun keeping the application 1102 of the light therapy device to be (a) prior to the current melatonin onset (now at 4 pm-5 pm) for 30-60 minutes, (b) at the same time as in FIG. 11 (from 12 pm-1 pm) for 15-30 minutes, and (c) at the desired wake time (at 6 am-8 am) for 15-30 minutes to reinforce this is the 'start' of the day. The light therapy regimen illustrated in FIG. 12 also indicates the patient should avoid 908 blue light immediately after the current melatonin peak continuously through the night (from 12 am-6 am).

FIG. 13 shows a third stage of a light therapy regimen where the portion of the light therapy regimen from FIG. 12 has adjusted the melatonin peak of the patient's circadian rhythm 902 to the preferred point (now between 2 am-3 am). An updated regimen of light therapy is established keeping the application 1102 of the light therapy device to be (a) prior to the current melatonin onset (now at 5 pm-8 pm) for 15-30 minutes and (b) at the desired wake time (at 6 am-8 am) for 15-30 minutes. The light therapy regimen illustrated in FIG. 13 also indicates the patient should avoid 908 blue light immediately before the current melatonin peak and continuously through the night (from 8 pm-6 am). In FIG. 13, the patient's circadian rhythm is now normalized. Going forward, patient can continue to monitor their circadian rhythm, using this light therapy regimen.

Additional Examples

The following is a non-exhaustive list of additional examples of the disclosed technology.

1. A method in a circadian rhythm entrainment platform, the method comprising:
  obtaining an indication of one or more medications for a patient;
  obtaining one or more circadian profiles for the one or more medications, wherein each circadian profile maps at least one of the one or more medications to one or more expected circadian rhythm changes;
  until a circadian rhythm condition for the patient has been met:
    determining a current circadian rhythm of the patient;
    determining a pre-treatment circadian rhythm adjustment based on the one or more circadian profiles and the current circadian rhythm of the patient;
    translating the pre-treatment circadian rhythm adjustment into a pre-treatment light therapy regimen; and
    causing an indication of the pre-treatment light therapy regimen to be conveyed via a device associated with the patient; and
  after the circadian rhythm condition for the patient has been met:
    determining a during-treatment circadian rhythm adjustment based on the one or more circadian profiles and an expected circadian rhythm of the patient;
    translating the during-treatment circadian rhythm adjustment into a during-treatment light therapy regimen; and
    causing an indication of the during-treatment light therapy regimen to be conveyed via the device associated with the patient.

2. The method of example 1 wherein:
  at least one of the one or more circadian profiles defines a pre-treatment circadian rhythm specifying what a patient's circadian rhythm should be before beginning an associated medication; and
  the pre-treatment circadian rhythm adjustment is a difference between the current circadian rhythm of the patient and the pre-treatment circadian rhythm.

3. The method of example 1 or example 2 wherein:
  the expected circadian rhythm of the patient is a measured circadian rhythm of the patient; and
  the during-treatment circadian rhythm adjustment is based on a difference between a normal circadian rhythm and the measured circadian rhythm of the patient; and the method further comprises:
    determining a post-treatment circadian rhythm adjustment based on a difference between a second expected circadian rhythm of the patient and the normal circadian rhythm;
    translating the post-treatment circadian rhythm adjustment into a post-treatment light therapy regimen; and
    causing an indication of the post-treatment light therapy regimen to be conveyed via the device associated with the patient.

4. The method of example 1 or example 2 wherein the during-treatment circadian rhythm adjustment is determined by:
  computing an uncompensated circadian rhythm that will result from applying the expected circadian rhythm changes to the expected circadian rhythm of the patient; and
  determining a difference between the uncompensated circadian rhythm and a normal circadian rhythm.

5. The method of any one of examples 1-4 wherein:
  the during-treatment circadian rhythm adjustment is a first during-treatment circadian rhythm adjustment determined based on a first circadian rhythm change identified in the one or more circadian profiles for a first stage in a course of the one or more medications; and
  the method further comprises:
    determining a second during-treatment circadian rhythm adjustment based on a second circadian rhythm change identified in the one or more circadian profiles for a second stage in the course of the one or more medications;
    translating the second during-treatment circadian rhythm adjustment into a second during-treatment light therapy regimen; and
    causing an indication of the second during-treatment light therapy regimen to be conveyed via the device associated with the patient.

6. The method of one or more of examples 1-5 wherein determining the pre-treatment circadian rhythm adjustment or determining the during-treatment circadian rhythm adjustment is based on a modifier for at least one of the one or more expected circadian rhythm changes, wherein the modifier specifies an expected circadian rhythm change based on the patient's age.

7. The method of one or more of examples 1-6 wherein the circadian rhythm condition comprises identifying that an updated current circadian rhythm of the patient is within a threshold amount of a pre-treatment circadian rhythm, wherein the pre-treatment circadian rhythm is based on the one or more circadian profiles.

8. The method of one or more of examples 1-6 wherein the circadian rhythm condition comprises identifying that the patient has completed the pre-treatment light therapy regimen.

9. A computer-readable storage medium storing instructions that, when executed by a computing system, cause the computing system to perform operations in a circadian rhythm entrainment platform, the operations comprising:
  obtaining an indication of one or more medications for a patient;
  obtaining one or more circadian profiles for the one or more medications, wherein each circadian profile maps at least one of the one or more medications to one or more expected circadian rhythm changes;
  determining one or more circadian rhythms of the patient;
  determining one or more during-treatment circadian rhythm adjustments based on the one or more circadian profiles and the one or more circadian rhythms of the patient;
  translating the one or more during-treatment circadian rhythm adjustments into one or more during-treatment light therapy regimens; and
  causing an indication of each of the one or more during-treatment light therapy regimens to be conveyed via a device associated with the patient.

10. The computer-readable storage medium of example 9 wherein the operations further comprise, prior to determining the one or more during-treatment circadian rhythm adjustments:
  determining a pre-treatment circadian rhythm adjustment based on the one or more circadian rhythms of the patient and a normal circadian rhythm; and
  translating the pre-treatment circadian rhythm adjustment into a pre-treatment light therapy regimen.

11. The computer-readable storage medium of one or more of examples 9-10 wherein the operations further comprise determining a medication administration schedule, for the indicated one or more medications, in which the one or more medications are expected to be most effective, wherein the medication administration schedule is based on:

the determined one or more circadian rhythms of the patient; and medication circadian effectiveness levels specified in the one or more circadian profiles, wherein the medication circadian effectiveness levels define points in patients' circadian rhythms where the one or more medications have been identified to be most effective.

12. The computer-readable storage medium of one or more of examples 9-11, wherein at least one of the one or more during-treatment circadian rhythm adjustments is determined by:

computing an uncompensated circadian rhythm that will result frond applying the expected circadian rhythm changes to the expected circadian rhythm of the patient; and determining a difference between the uncompensated circadian rhythm and a normal circadian rhythm.

13. The computer-readable storage medium of one or more of examples 9-12 wherein determining at least one of the one or more during-treatment circadian rhythm adjustments is based on a modifier of at least one of the one or more expected circadian rhythm changes that specifies an expected circadian rhythm change based on the patient's age.

14. The computer-readable storage medium of one or more of examples 9-13 wherein the indication of one or more medications for the patient is obtained through an interface with a medical provider of the patient.

15. A system comprising:
one or more processors;
a memory; and
circadian rhythm entrainment platform that, when executed by the one or more processors, causes the system to:

obtain an indication of one or more medications for a patient;

obtain one or more circadian profiles for the one or more medications, wherein each circadian profile maps at least one of the one or more medications to one or more circadian rhythm disruptions;

determine a during-treatment circadian rhythm adjustment based on the one or more circadian profiles and an expected circadian rhythm of the patient;

translate the during-treatment circadian rhythm adjustment into a during-treatment light therapy regimen; and cause an indication of the during-treatment light therapy regimen to be conveyed via a device associated with the patient.

16. The system of example 15 wherein:
execution of the circadian rhythm entrainment platform farther causes the system to obtain indications, associated with sleep or non-sleep, of biometrics or activity, for the patient; and the expected circadian rhythm of the patient is based on a mapping of the indications to a circadian rhythm for the patient.

17. The system of one or more of examples 15 or 16 wherein the during-treatment circadian rhythm adjustment is determined by:

computing an uncompensated circadian rhythm that will result from applying the expected circadian rhythm changes to the expected circadian rhythm of the patient; and determining a difference between the uncompensated circadian rhythm and a normal circadian rhythm.

18. A computer memory storing a data structure for use in a circadian rhythm entrainment platform, the data structure comprising:

identifications of one or more medications; and one or more mappings of the one or more medications to one or more corresponding expected changes in a patient's circadian rhythm, wherein the one or more mappings are based on observations of changes to circadian rhythms in patients when the patients are taring the one or more medications, and wherein the data structure is for use in the circadian rhythm entrainment platform to determine a light therapy regimen to offset side effects of the one or more medications.

19. The computer memory of example 18, further comprising one or more modifiers, each specifying an adjustment to the expected change in a patient's circadian rhythm for a particular context comprising one or more of:

an amount of the one or more medications prescribed;
a medication administration schedule;
interactions of the one or more medications with other medications;
patient age; or
any combination thereof.

20. The computer memory of one or more of examples 18 or 19 wherein the one or more mappings comprise a first mapping for a first stage in a course of the medication and a second mapping, specifying a different expected change in a patient's circadian rhythm from the first mapping, for a second stage in the course of the medication.

Conclusion

Several implementations of the disclosed technology are described above in reference to the figures. Those skilled in the art will appreciate that the components illustrated in the conceptual diagrams, examples, and flow diagrams discussed above may be altered in a variety of ways. For example, the order of the logic may be rearranged, sub-steps may be performed in parallel, illustrated logic may be omitted, other logic may be included, etc. In some implementations, one or more of the components described above can execute one or more of the described processes.

Reference in this specification to "implementations" or "embodiments" (e.g., "some implementations," "various implementations," "one embodiment," "an embodiment," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle-specified number of items, or that an item under comparison has a value within a middle-specified percentage range.

A "model," as used herein, refers to a construct that is trained using training data to make predictions or provide probabilities for new data items, whether or not the new data items were included in the training data. For example, training data can include items with various parameters (e.g., patient biometrics) and a known result (e.g., a circadian rhythm based on measured melatonin levels). A new data item can have parameters that a model can use to assign an expected result for the new data item, such as an expected circadian rhythm given biometric data. As another example, a model can be a probability distribution resulting from the analysis of training data, such as a likely shift amount occurring in a given circadian rhythm based on an analysis of a large number of identified shifts. Examples of models include: neural networks, support vector machines, decision trees, Parzen windows, Bayes, clustering, reinforcement learning, probability distributions, and others. Models can be configured for various situations, data types, sources, and output formats.

As used herein, the word "or" refers to any possible permutation of a set of items. For example, the phrase "A, B, or C" refers to at least one of A, B, C, or any combination thereof, such as any of A; B; C; A and B; A and C; B and C; A, B, and C; or multiple of any item such as A and A; B, B, and C; A, A, B, C, and C; etc.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow.

I claim:

1. A method in a circadian rhythm entrainment platform, the method comprising:
    obtaining an indication of one or more medications for a patient, wherein the one or more medications are known to affect the circadian rhythm of the patient;
    obtaining one or more circadian profiles for the one or more medications, wherein each circadian profile maps at least one of the one or more medications to one or more expected circadian rhythm changes;
    until a circadian rhythm condition for the patient has been met:
        determining a current circadian rhythm of the patient;
        determining a pre-treatment circadian rhythm adjustment based on the one or more circadian profiles and the current circadian rhythm of the patient;
        translating the pre-treatment circadian rhythm adjustment into a pre-treatment light therapy regimen; and
        causing an indication of the pre-treatment light therapy regimen to be conveyed via a mobile device associated with the patient; and
    after the circadian rhythm condition for the patient has been met:
        determining a during-treatment circadian rhythm adjustment based on the one or more circadian profiles and an expected circadian rhythm of the patient;
        translating the during-treatment circadian rhythm adjustment into a during-treatment light therapy regimen delivered to the patient via a dedicated light therapy device; and
        causing an indication of the during-treatment light therapy regimen to be conveyed via the device associated with the patient.

2. The method of claim 1 wherein:
    at least one of the one or more circadian profiles defines a pre-treatment circadian rhythm specifying what a patient's circadian rhythm should be before beginning an associated medication; and
    the pre-treatment circadian rhythm adjustment is a difference between the current circadian rhythm of the patient and the pre-treatment circadian rhythm.

3. The method of claim 1 wherein:
    the expected circadian rhythm of the patient is a measured circadian rhythm of the patient; and
    the during-treatment circadian rhythm adjustment is based on a difference between a normal circadian rhythm and the measured circadian rhythm of the patient; and
    the method further comprises:
    determining a post-treatment circadian rhythm adjustment based on a difference between a second expected circadian rhythm of the patient and the normal circadian rhythm;
    translating the post-treatment circadian rhythm adjustment into a post-treatment light therapy regimen; and
    causing an indication of the post-treatment light therapy regimen to be conveyed via the device associated with the patient.

4. The method of claim 1 wherein the during-treatment circadian rhythm adjustment is determined by:
    computing an uncompensated circadian rhythm that will result from applying the expected circadian rhythm changes to the expected circadian rhythm of the patient; and
    determining a difference between the uncompensated circadian rhythm and a normal circadian rhythm.

5. The method of claim 1 wherein:
    the during-treatment circadian rhythm adjustment is a first during-treatment circadian rhythm adjustment determined based on a first circadian rhythm change identified in the one or more circadian profiles for a first stage in a course of the one or more medications; and
    the method further comprises:
        determining a second during-treatment circadian rhythm adjustment based on a second circadian rhythm change identified in the one or more circadian profiles for a second stage in the course of the one or more medications;

translating the second during-treatment circadian rhythm adjustment into a second during-treatment light therapy regimen; and causing an indication of the second during-treatment light therapy regimen to be conveyed via the device associated with the patient.

6. The method of claim 1 wherein determining the pre-treatment circadian rhythm adjustment or determining the during-treatment circadian rhythm adjustment is based on a modifier for at least one of the one or more expected circadian rhythm changes, wherein the modifier specifies an expected circadian rhythm change based on the patient's age.

7. The method of claim 1 wherein the circadian rhythm condition comprises identifying that an updated current circadian rhythm of the patient is within a threshold amount of a pre-treatment circadian rhythm, wherein the pre-treatment circadian rhythm is based on the one or more circadian profiles.

8. The method of claim 1 wherein the circadian rhythm condition comprises identifying that the patient has completed the pre-treatment light therapy regimen.

9. A computer-readable storage medium storing instructions that, when executed by a computing system, cause the computing system to perform operations in a circadian rhythm entrainment platform, the operations comprising:

obtaining an indication of one or more medications for a patient, wherein the one or more medications are known to affect the circadian rhythm of the patient;

obtaining one or more circadian profiles for the one or more medications, wherein each circadian profile maps at least one of the one or more medications to one or more expected circadian rhythm changes;

determining one or more circadian rhythms of the patient;

determining one or more during-treatment circadian rhythm adjustments based on the one or more circadian profiles and the one or more circadian rhythms of the patient;

translating the one or more during-treatment circadian rhythm adjustments into one or more during-treatment light therapy regimens delivered to the patient via a dedicated light therapy device; and causing an indication of each of the one or more during-treatment light therapy regimens to be conveyed via a mobile device associated with the patient.

10. The computer-readable storage medium of claim 9 wherein the operations further comprise, prior to determining the one or more during-treatment circadian rhythm adjustments:

determining a pre-treatment circadian rhythm adjustment based on the one or more circadian rhythms of the patient and a normal circadian rhythm; and translating the pre-treatment circadian rhythm adjustment into a pre-treatment light therapy regimen.

11. The computer-readable storage medium of claim 9 wherein the operations further comprise determining a medication administration schedule, for the indicated one or more medications, in which the one or more medications are expected to be most effective, wherein the medication administration schedule is based on:

the determined one or more circadian rhythms of the patient; and medication circadian effectiveness levels specified in the one or more circadian profiles, wherein the medication circadian effectiveness levels define points in patients' circadian rhythms where the one or more medications have been identified to be most effective.

12. The computer-readable storage medium of claim 9, wherein at least one of the one or more during-treatment circadian rhythm adjustments is determined by:

computing an uncompensated circadian rhythm that will result from applying the expected circadian rhythm changes to the expected circadian rhythm of the patient; and determining a difference between the uncompensated circadian rhythm and a normal circadian rhythm.

13. The computer-readable storage medium of claim 9 wherein determining at least one of the one or more during-treatment circadian rhythm adjustments is based on a modifier of at least one of the one or more expected circadian rhythm changes that specifies an expected circadian rhythm change based on the patient's age.

14. The computer-readable storage medium of claim 9 wherein the indication of one or more medications for the patient is obtained through an interface with a medical provider of the patient.

15. A system comprising:

one or more processors;

a memory; and circadian rhythm entrainment platform that, when executed by the one or more processors, causes the system to:

obtain an indication of one or more medications for a patient, wherein the one or more medications are known to affect the circadian rhythm of the patient;

obtain one or more circadian profiles for the one or more medications, wherein each circadian profile maps at least one of the one or more medications to one or more circadian rhythm disruptions;

determine a during-treatment circadian rhythm adjustment based on the one or more circadian profiles and an expected circadian rhythm of the patient;

translate the during-treatment circadian rhythm adjustment into a during-treatment light therapy regimen delivered to the patient via a dedicated light therapy device; and cause an indication of the during-treatment light therapy regimen to be conveyed via a mobile device associated with the patient.

16. The system of claim 15 wherein:

execution of the circadian rhythm entrainment platform further causes the system to obtain indications, associated with sleep or non-sleep, of biometrics or activity, for the patient; and the expected circadian rhythm of the patient is based on a mapping of the indications to a circadian rhythm for the patient.

17. The system of claim 15 wherein the during-treatment circadian rhythm adjustment is determined by:

computing an uncompensated circadian rhythm that will result from applying the expected circadian rhythm changes to the expected circadian rhythm of the patient; and determining a difference between the uncompensated circadian rhythm and a normal circadian rhythm.

18. A computer memory storing a data structure for use in a circadian rhythm entrainment platform, the data structure comprising:

identifications of one or more medications known to affect circadian rhythms of a human patient; and one or more mappings of the one or more medications to one or more corresponding expected changes in the patient's circadian rhythm, wherein the one or more mappings are based on observations of changes to circadian rhythms in patients when the patients are taking the one or more medications, and wherein the data structure is for use in the circadian rhythm entrainment platform to determine a light therapy regimen, delivered to the patient via a dedicated light therapy device, to offset side effects of the one or more medications.

19. The computer memory of claim 18, further comprising one or more modifiers, each specifying an adjustment to the expected change in a patient's circadian rhythm for a particular context comprising one or more of:

an amount of the one or more medications prescribed;
a medication administration schedule;
interactions of the one or more medications with other medications;
patient age; or
any combination thereof.

20. The computer memory of claim 18 wherein the one or more mappings comprise a first mapping for a first stage in a course of the medication and a second mapping, specifying a different expected change in a patient's circadian rhythm from the first mapping, for a second stage in the course of the medication.

* * * * *